United States Patent
Zhou et al.

(10) Patent No.: US 7,096,167 B2
(45) Date of Patent: Aug. 22, 2006

(54) SYSTEM AND METHOD FOR MOLECULAR DYNAMIC SIMULATION

(75) Inventors: Ruhong Zhou, Fort Lee, NJ (US);
Bruce J. Berne, Irvington, NY (US);
Edward Harder, New York, NY (US);
Huafeng Xu, Cranbury, NJ (US)

(73) Assignee: International Business Machines Corporation, Armonk, NY (US)

( * ) Notice: Subject to any disclaimer, the term of this patent is extended or adjusted under 35 U.S.C. 154(b) by 846 days.

(21) Appl. No.: 10/131,183

(22) Filed: Apr. 25, 2002

(65) Prior Publication Data

US 2003/0014231 A1 Jan. 16, 2003

Related U.S. Application Data

(60) Provisional application No. 60/287,093, filed on Apr. 26, 2001.

(51) Int. Cl.
*G06F 17/10* (2006.01)
*G06G 7/48* (2006.01)
(52) U.S. Cl. .................................. 703/2; 703/6; 702/19
(58) Field of Classification Search .................... 703/2, 703/6; 702/19

See application file for complete search history.

(56) References Cited

OTHER PUBLICATIONS

Stuart et al.; Molecular dynamics with multiple time scales: the selection of efficient reference system propagators; JCP; pp. 1426-1436; 1996.*
Deserno et al.; How to mesh up Ewald sums. ! A theoretical and numerical comparison of various particle mesh routines; JCP; pp. 7678-76-93; 1998.*

* cited by examiner

*Primary Examiner*—Hugh Jones
(74) *Attorney, Agent, or Firm*—Jesse L. Abzug, Esq.; McGinn IP Law Group, PLLC

(57) ABSTRACT

A system and method for molecular dynamic simulation includes a database for storing data pertaining to at least one biomolecular system, a memory device for storing instructions for performing at least one algorithm having an electrostatic interaction calculating function and a multiple time step function, and subdividing forces on a basis of distance over which the forces act, and a processor for processing the data by executing the instructions in order to propagate the biomolecular system from a first set of coordinates to a second set of coordinates. The system and method significantly speed up the molecular dynamics simulation of biomolecular systems in which there are long-range and short-range electrostatic interactions and in which there are fast and slow motions, and make practicable the simulation of large protein solutions and thus, can be used to simulate protein folding and the binding of substrates to protein molecules.

27 Claims, 10 Drawing Sheets

Table I

| SYSTEM | PROTEIN SIZE | NET CHARGE | IONS | WATER BOX | TOTAL SIZE |
|---|---|---|---|---|---|
| hairpin | 256 | 3− | 3 Na+ | 30.0 | 2521 |
| 2gb1 | 855 | 4− | 4 Na+ | 36.0 | 4276 |
| 1orc | 1181 | 3+ | 3 Cl− | 42.0 | 6911 |
| 121p | 2619 | 8− | 8 Na+ | 50.0 | 11717 |
| 1akz | 4128 | 5+ | 5 Cl− | 55.0 | 15704 |
| 8abp | 4674 | 3− | 3 Na+ | 62.0 | 22716 |
| 1feh | 11238 | 4− | 4 Na+ | 84.0 | 56929 |

Table II

| METHOD | {n} | Δt | log(ΔE) | $T_{total}$ |
|---|---|---|---|---|
| Ewald/Verlet | — | 1.0 | -3.22 | 25.11 |
|  | — | 2.0 | -1.98 | 12.65 |
|  | — | 3.0 | —* |  |
| Ewald/RESPA1 | (2,2,2) | 4.0 | -3.56 | 8.073 |
|  | (2,2,3) | 6.0 | -3.04 | 5.668 |
|  | (2,2,4) | 8.0 | -2.21 | 4.338 |
|  | (2,3,3) | 9.0 | -1.97 | 3.987 |
| Ewald/RESPA2 | (2,2,2) | 4.0 | -3.72 | 7.358 |
|  | (2,2,3) | 6.0 | -3.59 | 4.670 |
|  | (2,2,4) | 8.0 | -3.31 | 3.781 |
|  | (2,3,3) | 9.0 | -3.12 | 3.173 |
|  | (2,3,4) | 12.0 | -2.72 | 2.540 |

FIG.6

Table III

| METHOD | {n} | Δt | log(ΔE) | $T_{total}$ |
|---|---|---|---|---|
| P3ME/Verlet | — | 1.0 | -3.20 | 4.386 |
|  | — | 2.0 | -2.02 | 2.210 |
|  | — | 3.0 | —* |  |
| P3ME/RESPA1 | (2,2,2) | 4.0 | -3.55 | 2.012 |
|  | (2,2,3) | 6.0 | -3.07 | 1.333 |
|  | (2,2,4) | 8.0 | -2.22 | 1.139 |
|  | (2,3,3) | 9.0 | -1.99 | 0.9187 |
| P3ME/RESPA2 | (2,2,2) | 4.0 | -3.70 | 1.901 |
|  | (2,2,3) | 6.0 | -3.61 | 1.172 |
|  | (2,2,4) | 8.0 | -3.32 | 1.010 |
|  | (2,3,3) | 9.0 | -3.12 | 0.9094 |
|  | (2,3,4) | 12.0 | -2.69 | 0.7817 |

FIG.7

SYSTEM AND METHOD FOR MOLECULAR DYNAMIC SIMULATION

CROSS REFERENCES TO RELATED APPLICATIONS

This Application claims the benefit of U.S. Provisional Application No. 60/287,093 which was filed on Apr. 26, 2001 by Ruhong Zhou, et al. and assigned to the present assignee, and which is incorporated herein by reference.

BACKGROUND OF THE INVENTION

1. Field of the Invention

The present invention generally relates to a system and method for molecular dynamic simulation, and more particularly, to a system and method for molecular dynamic simulation which may use an algorithm having an electrostatic interaction calculating function (e.g., Ewald, particle mesh Ewald (PME), etc.) and a multiple time step function (e.g., reversible reference system propagator (RESPA, etc.)) to propagate a protein system from one set of coordinates to another in conformation space.

2. Description of the Related Art

Molecular dynamics simulations of all-atom models of proteins in water are of great current interest (J. A. McCammon and S. C. Harvey, *Dynamics of Proteins and Nucleic Acids* (Cambridge University Press, Cambridge, 1987); K. M. Merz, Jr. and S. M. LeGrand, *The Protein Folding Problem and Tertiary Prediction* (Birkhauser, Boston, 1994); J. Gunn and R. A. Friesner, Annu. Rev. Biophys. Biomol. Struct. 25. 315 (1996)). To elucidate protein folding pathways, for example, it will be necessary to simulate trajectories of duration longer than 1 microsecond (K. M. Merz, Jr. and S. M. LeGrand, *The Protein Folding Problem and Tertiary Structure Prediction* (Birkhauser, Boston, 1994)).

The long-range electrostatic forces in biomolecular systems make such simulations computationally intensive and lead to computational bottlenecks. Further, the dynamics in such systems usually have multiple time scales. The fast motions typical of the vibrations of intramolecular bonds require small (e.g., sub-femtosecond) time steps for stable integration of the equations of motion, and after propagating each short time step, all of the forces, including the long-range forces, must be recalculated. Since the calculation of the long-range forces is the most CPU intensive part of molecular dynamics, minimizing this part of the computational effort can lead to a great reduction of the computational cost. For this reason, considerable effort has been expended in devising methods for reducing the frequency with which the long-range forces must be recalculated, and reducing the computational effort required to compute these forces themselves.

One way to reduce the large computational cost associated with all-atom simulations is to use implicit solvent models, such as the generalized Born (GB) model, (W. C. Still, A. Tempczyk, R. C. Hawley, and T. Hendrickson, J. Am. Chem. Soc. 112, 6127 (1990)), together with stochastic dynamics with terms representing solvent friction. These models often generate very useful and interesting insights for protein folding, but it is generally difficult, if not impossible, to generate trustworthy chemical kinetic or transport information from this approach.

For realistic simulations of protein folding dynamics, all atom-based models with explicit solvent will be required. One method for reducing the computational costs of calculating the long-range forces in all-atom models is to truncate them with a spherical or minimum image truncation. This approach is very common in the literature. Unfortunately, spherical truncation or minimum image truncation is known to give rise to unphysical effects (M. Belhadj, H. E. Alper, and R. M. Levy, Chem. Phys. Lett, 179, 13 (1991); D. M. York, T. A. Darden, and L. G. Pedersen, J. Chem. Phys. 99, 8345 (1993)), and it is now widely recognized that one should not truncate the long-range electrostatic forces.

The conventional Ewald method for calculating the full Coulomb interaction in periodic systems without truncation has computational complexity that is at least of order $O(N^{3/2})$. To speed up the calculation of these periodic long-range electrostatic forces, two general classes of more efficient algorithms have been developed: one is the fast multipole methods (FMM), first proposed by Greengard et al. (L. Greengard, *The Rapid Evaluation of Potential Fields in Particle Systems* (MIT Press, Cambridge, Mass., 1998)) and then extended to periodic systems by Francisco et al. (F. Figueirido, R. Zhou, R. Levy, and B. J. Berne, J. Chem. Phys. 106, 9835 (1997), which scales as $O(N)$; and the other is the mesh-based Ewald methods (such as PME or the equivalent P3ME variants based on the original work of Hockney) which interpolate the point charges onto a mesh and then utilize the fast Fourier transform (FFT) to speed up the reciprocal space evaluation in the Ewald sum. These mesh-based methods scale as $O(N \log N)$. Despite the improved computational complexity of the FMM or mesh-based methods, the conventional Ewald method gives superior accuracy in determining the electrostatic forces and potentials.

Deserno and Holm (M. Deserno and C. Holm, J. Chem. Phys., 109, 7678 (1998)), have written a comprehensive and thoughtful analysis of various mesh-based Ewald methods. They compared the particle-particle particle-mesh Ewald method (or P3ME method) of Luty et al. (B. A. Luty, I. G. Tironi, and W. F. van Gunsteren, J. Chem. Phys. 103, 3014 (1995)), with the particle mesh Ewald (PME) method of Darden and with the smoothed particle mesh Ewald (or SPME) method of Essmann et al. (U. Essmann, L. Perera, M. L. Berkowitz, T. Darden, H. Lee, and L. G. Pedersen, J. Chem. Phys. 103, 8577 (1995)), and concluded that both P3ME and SPME are considerably more accurate than PME method, and that the P3ME method is slightly more accurate than the SPME method for the same number of mesh points.

To reduce the frequency with which the long-range electrostatic forces are calculated, the reversible RESPA (r-RESPA) method (M. Tuckerman, B. J. Berne, and G. J. Martyna, J. Chem. Phys. 97, 1990 (1992)) proves very helpful. Further, in a previous publication (S. J. Stuart, R. Zhou, and Bruce J. Berne, J. Chem. Phys. 105, 1426 (1996)), a method for combining Ewald with RESPA was described. However, in that paper it is shown that a subdivision of the force, in which the real-space part of the force was included in the inner loop of r-RESPA, whereas the Fourier space part was combined into the outer loops, was inefficient. This followed because the Fourier space part contains contributions to the force which vary rapidly in time. These fast parts of the Fourier space contribution restrict the choice of the outer loop time step and thus lead to more frequent calculations of the Fourier space part than necessary.

Unfortunately, the inefficient Ewald r-RESPA strategy was adopted by others. For example, this strategy was used by Procacci et al. to combine Ewald with RESPA (P. Procacci and M. Marchi, J. Chem. Phys. 104, 3003 (1996)), and later to combine particle mesh Ewald (PME) with RESPA (P. Procacci, T. Darden, and M. Marchi, J. Phys.

Chem. 100, 10464 (1996)). In this strategies, real space/reciprocal space decomposition was still used for the electrostatic forces. The Fourier, or reciprocal space (k-space), forces in PME were put in the middle of a three-level (near, medium, and long) distance-based real-space force decomposition, which leads to the real long-ranged k-space contributions being updated too often (even more often than the "long"-range real-space forces), and the short-ranged k-space contributions being updated not often enough.

SUMMARY OF THE INVENTION

In view of the foregoing and other problems, disadvantages, and drawbacks of the conventional systems and methods, the present invention has been devised having as its objective, to provide a system and method for fast and accurate molecular dynamic simulation.

Generally, the inventive system 100 shows how a specific subdivision of the real space and Fourier space (k-space) forces leads to a larger time step in a multiple time step algorithm (e.g., RESPA) than the conventional subdivision. For instance, for systems ranging from 2,500 atoms to 50,000 atoms, the inventors showed that the new subdivision with Ewald gave a factor of 6–8 improvement over a standard algorithm Verlet, while the old subdivision only gave a factor of 3–5 for the same accuracy, a comparison which should improve with even larger system sizes. Thus, the new subdivision scheme roughly doubles the speed compared to the old subdivision scheme.

The present invention includes a system for molecular dynamic simulation which includes a database for storing data pertaining to at least one biomolecular system, and a memory device for storing instructions for performing at least one algorithm. The algorithm should include an electrostatic interaction (e.g., short-range and/or long-range electrostatic force) calculating function and a multiple time step function (e.g., RESPA), and subdivide forces based on distances over which the forces act. Further, the system includes a processor for processing the data by executing the instructions in order to propagate the protein systems or other biomolecular systems.

In addition, the inventive system may also include a display device for displaying information (e.g., the generated representation). The system may also include an input device for inputting information such as data pertaining to a biomolecular system or instructions for processing the data.

The inventive system uses a different breakup of the electrostatic forces than is used by conventional systems which, for example, combine the Particle Mesh Ewald method with RESPA. The inventors discovered that he breakup in conventional systems is inefficient because it treats the reciprocal space forces in an outer loop even though these forces contain a part that changes rapidly in time. This does not allow the use of a large time step for the outer loop. The inventive system, on the other hand, captures the short-range contributions in the reciprocal space forces and includes them in the inner loop, thereby allowing for larger outer loop time steps and, thus, for a much more efficient multiple time step (e.g., RESPA) implementation. Further, the inventive system has been applied to both regular Ewald and P3ME.

More specifically, the forces may be subdivided on a basis of distance over which said forces act regardless of whether said forces are from real-space or k-space forces. For example, the algorithm may include a first portion which separates long-range contributions to reciprocal space forces from short range contributions thus making the modified "k-space" truly long-range force (slow force), and a second portion which performs further force decomposition based on pair distances for the modified short-range "real space" force (fast force).

In particular, the algorithm may compute a sum of short range electrostatic interactions by the equation $$V_{ij}^0 = (1-\delta_{ij})q_iq_j\frac{1}{r_{ij}}h(r_{ij}),$$

where $\delta_{ij}$ is the Dirac delta function with the value of 1 if i=j, and 0 otherwise, $q_i$ and $q_j$ are charges associated with particles i and j, respectively, $r_{ij}$ is pair distance between particles i and j, and $h(r_{ij})=1$ if $x \leq L/2$ and $h(r_{ij})=0$ if $x \geq L/2$, where L is a minimum image cutoff (cutoff=L/2).

The algorithm may also compute a sum of long range electrostatic interactions by the equation $$V_{ij}^n = q_iq_j\left[-(1-\delta_{ij})\frac{\text{erf}(\alpha r_{ij})}{r_{ij}}h(r_{ij}) + \frac{1}{\pi L^3}\sum_{k\neq 0}\frac{4\pi^2}{k^2}e^{-k^2/4\alpha^2}\cos(k\cdot r_{ij}) - \delta_{ij}\frac{2\alpha}{\sqrt{\pi}}\right],$$

where $q_i$ and $q_j$ are charges associated with particles i and j, respectively, $\delta_{ij}$ is the Dirac delta function with a value of 1 is i=j, and 0 otherwise, $\alpha$ is a screening parameter, $r_{ij}$ is pair distance, and $h(r_{ij})=1$ if $x \leq L/2$ and $h(r_{ij})=0$ if $x \geq L/2$, where L is a minimum image cutoff, and k is k-space vector magnitude. Further, the algorithm may compute a full pair potential by the equation $$V_{ij}^{el} = V_{ij}^0 + V_{ij}^n$$

where $V_{ij}^0$ is the sum of the short range electrostatic interactions and $V_{ij}^n$ is the sum of the long range electrostatic interactions.

More specifically, the algorithm may include an Ewald and reversible reference propagator (Ewald/RESPA) algorithm, or a particle-particle particle-mesh Ewald and reversible reference propagator (P3ME/RESPA) algorithm. The force decomposition technique described above for Ewald/RESPA is equally applicable to P3ME/RESPA.

In another aspect of the present invention, an inventive method for molecular dynamic simulation includes storing data pertaining to at least one biomolecular system and instructions for performing at least one algorithm having an electrostatic interaction calculating function and a multiple time step function. Further, the algorithm subdivides forces on a basis of distances over which the forces act. The inventive method also includes processing the data by executing the instructions in order to propagate the protein systems.

Alternatively, the inventive method for molecular dynamic simulation may include separating bonded interactions from non-bonded interactions using a multiple time step algorithm, separating the non-bonded interactions into short-range, midrange, and long-range interactions using the multiple time step algorithm, using a P3M algorithm to calculate magnitudes of long-range electrostatic interactions, and combining calculated long-range electrostatic interactions with the multiple time step algorithm to propagate the protein system.

The present invention also includes a programmable storage medium tangibly embodying a program of machine-readable instructions executable by a digital processing apparatus to perform the inventive method.

With its unique and novel features, the present invention provides a fast and accurate molecular dynamics simulation system and method. Unlike conventional algorithms which subdivide the Ewald or P3ME electrostatic forces into traditional real-space and k-space forces and then treat the forces as short-range (fast) and long-range (slow) forces, the present invention combines the force calculating function and multiple time step function (e.g., Ewald and RESPA) in an optimal way by "squeezing" the short-range contributions out of the k-space forces, thus making the modified "k-space" forces truly long-range (slow). This results in less computation time and a much more efficient system than conventional systems.

BRIEF DESCRIPTION OF THE DRAWINGS

The foregoing and other objects, aspects and advantages will be better understood from the following detailed description of a preferred embodiment of the invention with reference to the drawings, in which:

FIG. 6 provides Table II which lists the detailed results for Ewald's combination with the two RESPA approaches;

FIG. 7 provides Table III which lists the CPU and energy conservation results for 8 abp using the P3ME method;

DETAILED DESCRIPTION OF PREFERRED EMBODIMENTS OF THE INVENTION

Figures 1, 2:
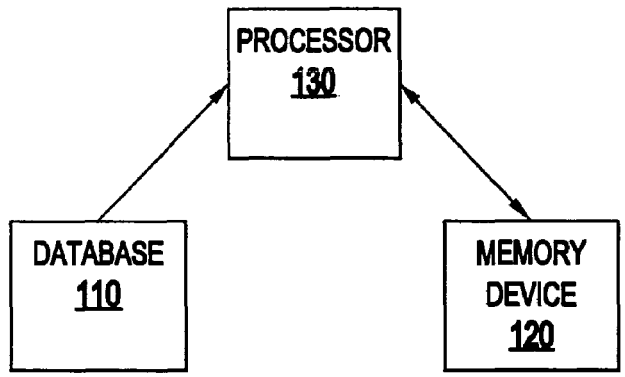
FIG. 1 is a schematic diagram of an inventive system 100 according to the present invention.
FIG. 2 provides Table I which explains the protein systems used in the inventors' experiments.

Referring now to the drawings, FIG. 1 illustrates an inventive system 100 for molecular dynamic (MD) simulation.

In the inventive system 100, the particle-particle particle-mesh (P3M) method for calculating long-range electrostatic forces in molecular simulations may be modified and combined with the reversible reference system propagator algorithm (RESPA) for treating the multiple time scale problems in the molecular dynamics of biomolecular systems (e.g., complex systems) with multiple time scales and long-range forces. The inventive system 100 (e.g., particle-particle particle-mesh Ewald RESPA (P3ME/RESPA)) provides a fast and accurate representation of the long-range electrostatic interactions for biomolecular systems such as protein solutions.

Specifically, the inventive system 100 uses a different breakup of the electrostatic forces than was used by conventional systems which combined the Particle Mesh Ewald method with RESPA. The breakup in conventional systems is inefficient because it treats the reciprocal space forces in an outer loop even though they contain a part that changes rapidly in time. This does not allow use of a large time step for the outer loop.

The inventive system 100, on the other hand, captures the short-range contributions in the reciprocal space forces and includes them in the inner loop, thereby allowing for larger outer loop time steps and, thus, for a much more efficient RESPA implementation.

The inventive system 100 has been applied to both regular Ewald and P3ME. Further, the inventors conducted experiments to compare in detail the timings of Ewald/RESPA and P3ME/RESPA with the conventional systems for protein water solutions as a function of number of atoms in the system and found that the inventive system 100 is significantly faster than the conventional systems.

As noted above, both P3ME and SPME are considered more accurate than PME method, and the P3ME method is slightly more accurate than the SPME method for the same number of mesh points. For this reason, the inventors used P3ME, even though the differences between the two methods are very small.

Referring again to FIG. 1, the inventive system 100 includes a database 110 for storing data pertaining to at least one biomolecular system, a memory device 120 for storing instructions for performing at least one algorithm having an electrostatic interaction calculating function and a reversible reference system propagator (RESPA) function, and a processor 130 for processing said data by executing said instructions in order to generate a representation of electrostatic interactions.

The inventive system 100 may also include, for example, a display device for displaying the representation generated by the processor 130, or a printer for printing the representation. Further, the inventive system 100 may include an input device (e.g., a keyboard, mouse, etc.) for inputting data (e.g., data pertaining to biomolecular systems), instructions (e.g., instructions to be executed by the process for performing a predetermined algorithm), or other information into the system 100. In addition, the input device may be used to input data which is generated by the user, or downloaded from another database such as a public database to the inventive system 100.

Further, the memory device 120 may include, for example, RAM, ROM, etc.) and store instructions for processing data. Specifically, the memory device 120 may store instructions for performing at least one algorithm having an electrostatic interaction calculating function and a multiple time step function (e.g., reversible reference system propagator (RESPA) function). For instance, the algorithm may include an Ewald and reversible reference propagator (Ewald/RESPA) algorithm (e.g., a combined Ewald/RESPA algorithm), and/or a combined particle-particle particle-mesh Ewald and reversible reference propagator (P3ME/RESPA) algorithm. In addition, the memory device 120 may be used to store other data, such as data (e.g., data pertaining to a representation of the electrostatic interactions in the biomolecular system) which may be, for example, generated by the processor 130.

Further, data to be processed by the processor 130 may be stored in the database 130 or downloaded from another database (e.g., a remote database) via the World Wide Web (e.g., Internet) into the memory device 120. In other words, the data to be processed by the inventive system 100 does not necessarily have to be permanently stored therein, but may instead be downloaded by the inventive system 100 for the purposes of processing. In addition, the memory device 120 may also store the data to be processed (e.g., instead of storing the data in a separate database).

Further, the processor 130 (e.g., a microprocessor, central processing unit (CPU), etc.) may be used to process the data which is input into the inventive system 100. For example, the processor 130, may process data (e.g., data stored in the database 110 or other memory device, or downloaded from the Internet) by executing instructions for performing a predetermined algorithm in order to generate a representation of electrostatic interactions.

Generating a Representation

The inventive system 100 uses a very efficient algorithm for treating all-atom molecular dynamics in systems, like aqueous protein systems, which have long-range forces and multiple time scales. The inventive system 100 may also be used in molecular dynamics simulations of complex materials.

Specifically, to overcome the bottlenecks in MD simulations due to multiple time scales and long-range forces, the inventive system 100 may combine the r-RESPA (M. Tuckerman, B. J. Berne, and G. J. Martyna, J. Chem. Phys. 97, 1990 (1992)), multiple time step method with the P3ME method. The basic strategy for subdividing the forces in systems with Ewald boundary conditions, as suggested in a paper by Stuart et al. (S. J. Stuart, R. Zhou, and Bruce J. Berne, J. Chem. Phys. 105, 1426 (1996)), may be utilized in the inventive system 100 in the P3ME method and obviously can be readily applied to the PME method as well, since P3M and PME are very similar.

The inventors have combined the inventive subdivision of the forces with Ewald and P3ME and used it for timings on several different protein solutions. The inventors compared the inventive system 100 and old strategies to show that the inventive system 100 gives significant improvements in speed. In addition, the inventive system 100 works equally well with the PME method.

Combining an Electrostatic Interaction Function and a Multiple Time Step Function Multiple-time scale methods such as r-RESPA are based on subdividing the interparticle forces into a hierarchy ranging from the fastest to the slowest parts. This allows the more slowly varying forces to be integrated with a fairly long time step, while still using smaller time steps for the forces which change more rapidly. This results in faster simulation speeds than are obtainable using single-time step methods, and the time savings can be used to study larger systems, for longer simulation times. This increase in efficiency springs from the fact that the slowest parts of the force (usually the longest-range part of the force field) is recalculated after the largest time step rather than after the short time steps used in conventional methods. Various implementations of the r-RESPA method have been applied to a wide variety of systems, resulting in speedups by factors of 4 to 15.

The choice of how to subdivide the forces is very important, and the most useful split is often dictated by the physics of the problem at hand. Occasionally, however, several different choices seem appropriate, and sometimes the most obvious factorization does not turn out to be the most efficient. Thus, one aim of the inventors was to outline the most efficient split for systems with long-range electrostatic forces treated by Ewald summation. The inventors also adopted this strategy for more complex systems such as protein solutions using mesh-based methods such as P3ME and PME, which are described in more detail below.

It should be noted that "long-range" forces and "short-range" may be identified by reference to a pair distance, $r_{ij}$. That is, where a pair distance, $r_{ij}$, is larger than a certain value, the force may be considered a long-range force, and where a pair distance, $r_{ij}$ is smaller than a certain value, the force may be considered a short-range force. Further, a long-range force may be considered a "slow force" (e.g., a force that varies slowly with time) so that a longer time step can be used, and a short-range force may be considered a "fast force" (e.g., a force which varies fast with time) so that a short time step must be used.

Further, whether a force is considered a long-range, medium-range, or short-range force may vary depending upon the system being analyzed. For example, for a protein/water system having about 100,000 atoms, long, medium and short range forces may be considered as being greater than 12 Å, 6–10 Å and less than 6 Å, respectively, whereas in a protein/water system having 30,000 atoms, long, medium and short range forces may be considered as being greater than 10 Å, 6–10 Å and less than 6 Å, respectively, and in a protein/water system having 5,000 atoms, long, medium and short range forces may be considered as being greater than 9 Å, 6–9 Å and less than 6 Å, respectively.

For a system which interacts through pairwise additive forces, if one can subdivide the force $F_{ij}$ between particles i and j into fast $F^{(f)}_{ij}$ and slow $F^{(s)}_{ij}$ parts, such that $$F^{(s)}_{ij} - F^{(f)}_{ij} = F_{ij}. \quad (1)$$

the r-RESPA integrator corresponding to the Verlet velocity may be given as (S. J. Stuart, R. Zhou, and Bruce J. Berne, J. Chem. Phys. 105. 1426 (1996)), $$v = v + F^{(s)} \frac{\Delta t}{2m}$$

$$\text{do } i = 1, n$$

-continued $$v = v + F^{(f)}\frac{\delta t}{2m}$$

$$x = x + v\delta t$$

$$v = v + F^{(f)}\frac{\delta t}{2m}$$

end do $$v = v + F^{(s)}\frac{\Delta t}{2m}.$$

Note that while the velocities will be updated on two different time scales, the positions will be updated using only the smallest time step. This type of RESPA algorithm is referred to as a force-based split.

The above may be applied to a simple system, such as a periodic box containing charged Lennard-Jones particles, using Ewald summation (the same approach can be used for more complex systems such as protein solutions, as show below). Since Ewald sums are used to evaluate long-ranged Coulombic interactions, it seems natural to use them as a basis for separating near (fast) and far (slow) forces in a RESPA split. A straightforward application of this idea does indeed provide a noticeable speedup (P. Procacci and M. Marchi, J. Chem. Phys. 104, 3003 (1996)), but as suggested before (S. J. Stuart, R. Zhou, and Bruce J. Berne, J. Chem. Phys. 105, 1426 (1996)), a less obvious split provides for an even more efficient propagator.

In general, the technique of Ewald sums (P. Ewald, Ann. Phys. (Leipzig) 64, 253, (1921)), is useful in systems with large partial charges, since the long-ranged Coulomb interactions do not converge sufficiently when summed over a single unit cell. The slowly (and conditionally) converging sum of electrostatic interactions $$V^{el} = \frac{1}{2}\sum_n\sum_i\sum_j{}' \frac{q_i q_j}{|r_{ij}+nL|} \quad (2)$$

is rearranged so that part of it is summed in real space, and the rest is summed in Fourier space (D. M. Heyes, J. Chem. Phys. 74, 1924 (1981)), $$V^{el} = \frac{1}{2}\sum_i\sum_{j\neq i} q_i q_j \frac{\text{erfc}(\alpha r_{ij})}{r_{ij}} + \quad (3)$$
$$\frac{1}{2}\sum_i\sum_j\sum_{k\neq 0}\frac{1}{\pi L^3}\frac{4\pi^2}{k^2}q_i q_j e^{-k^2/4\alpha^2}\cos(k\cdot r_{ij}) - \frac{\alpha}{\sqrt{\pi}}\sum_i q_i^2$$

where the metallic boundary condition is used.

With a suitable choice for the screening parameter, α, both sums can be made to converge reasonably quickly (D. Fincham, Mol. Simul. 13, 1 (1994)). More specifically, α is generally chosen so that the first term in the expression above (the real-space sum) is adequately converged within a radius of no more than r=L/2, where L is the side length of the cubic unit cell. Therefore, the first term includes primarily short-ranged interactions. The second term (k-space sum), on the other hand, results from a Fourier expansion of the potential due to an infinite array of Gaussian charges, much of which is considerably longer-ranged than the real-space sum. Under the usual assumption that long-ranged forces may be updated less frequently than short-ranged forces, it may thus seem reasonable to separate the real- and k-space sums in a RESPA split. For example, if the Ewald sum is rewritten in the form $$V^{el} = \frac{1}{2}\sum_i\sum_j V_{ij}^{el}, \quad (4)$$

where $$V_{ij}^{el} = \quad (5)$$
$$q_i q_j \left[(1-\delta_{ij})\frac{\text{erfc}(\alpha r_{ij})}{r_{ij}} + \frac{1}{\pi L^3}\sum_{k\neq 0}\frac{4\pi^2}{k^2}e^{-k^2/4\alpha^2}\cos(k\cdot r_{ij}) - \delta_{ij}\frac{2\alpha}{\sqrt{\pi}}\right],$$

then the real-space and k-space parts of the potential can be separated $$V_{ij}^{el} = V_{ij}^{rs} + V_{ij}^{ks}, \quad (6)$$

with $V_{ij}^{rs} = (1-\delta_{ij})q_i q_j \frac{\text{erfc}(\alpha r_{ij})}{r_{ij}} \quad (7)$ and $V_{ij}^{ks} = q_i q_j \left[\frac{1}{\pi L^3}\sum_{k\neq 0}\frac{4\pi^2}{k^2}e^{-k^2/4\alpha^2}\cos(k\cdot r_{ij}) - \delta_{ij}\frac{2\alpha}{\sqrt{\pi}}\right]. \quad (8)$ With these definitions, a RESPA split may be defined by $$F^{(f)}{}_{ij} = -\nabla r_{ij} V^{rs}{}_{ij} + F^{LJ}{}_{ij} \quad (9)$$

where $F^{LJ}{}_{ij}$ is the short range Lennard-Jones Force, and $$F^{(s)}{}_{ij} = -\nabla r_{ij} V^{ks}{}_{ij} \quad (10)$$

and the r-RESPA integrator may be used to propagate the dynamics (the real-space forces could also be further subdivided into distance classes, if desired). Such an approach seems perfectly reasonable, given the disparity in distances over which the terms in the real- and k-space sums act. Indeed, an approach very similar to this has been used recently in large-scale Ewald simulations of proteins (P. Procacci and M. Marchi, J. Chem. Phys. 104, 3003 (1996)).

However, although this particular RESPA split is moderately successful, the inventors have discovered that it is not necessarily the best choice. The reason for this is that the "long-ranged" k-space sum still contains some fraction of every pair interaction, even the most short-ranged. This can be seen by re-expressing Eq. (2) as $$V^{el} = \frac{1}{2}\sum_n\sum_i\sum_j{}' \frac{q_i q_j}{|r_{ij}+nL|}[\text{erfc}(\alpha|r_{ij}+n|)] + \text{erf}(\alpha|r_{ij}+nL|)] \quad (11)$$

where the following identity $$\text{erfc}(x) + \text{erf}(x) = 1 \quad (12)$$

has been used in Eq. (2). For typical values of the screening parameter α, the erfc (α|r$_{ij}$+n|) decays to zero so quickly that interactions between particles in different primary cells can be ignored, thereby taking n=0 in the sum with the complimentary error functions. Comparison of Eq. (11) with Eq. (3)

shows that the reciprocal space part given in Eq. (8) implicitly contains the erf($\alpha|r_{ij}+n|$) terms. As explained below, this function will vary strongly with $r_{ij}$ when $|r_{ij}|\approx\alpha^{-1}$.

Thus, the breakup of the forces suggested in Eqs. (9) and (10) is not optimal as the reciprocal space part of the force will vary rapidly for pairs that are close to each other. The presence of these short-ranged interactions in the k-space sum will limit the size of the large time step At more than would be necessary if the slow piece of the propagator were truly long-ranged. Indeed, in the published report which uses this propagator, the k-space forces required a time step which was shorter than that used for some of the real-space forces (P. Procacci and M. Marchi, J. Chem. Phys. 104, 3003 (1996)).

The inventors have discovered that a better alternative would be to remove the fast part of the erf(x) contributions from the reciprocal space terms in Eq. (8) and add it to the real-space term in Eq. (7). The term to be subtracted and added is $$\Delta = (1-\delta_{ij})\frac{q_i q_j}{r_{ij}}\text{erf}(\alpha r_{ij})h(r_{ij}) \qquad (13)$$

where h(x) is defined such that h(x)=1 if $x\leq L/2$ and h(x)=0 if $x\geq L/2$, where L/2 is a minimum image cutoff. Adding $\Delta$ into Eq. (7), and substituting the identity given in Eq. (12) into the resulting equation allows us to write the new real-space part containing the rapidly varying part of the potential as $$V_{ij}^0 = (1-\delta_{ij})q_i q_j \frac{1}{r_{ij}}h(r_{ij}) \qquad (14)$$

It should be noted that Eq. (14) is equivalent to the usual minimum image real space energy with a short-range cutoff.

In place of the reciprocal space contribution to the energy, a potential contribution that varies slowly with pair separations is obtained $$V_{ij}^n = q_i q_j \left[ -(1-\delta_{ij})\frac{erf(\alpha r_{ij})}{r_{ij}}h(r_{ij}) + \frac{1}{\pi L^3}\sum_{k\neq 0}\frac{4\pi^2}{k^2}e^{-k^2/4\alpha^2}\cos(k\cdot r_{ij})-\delta_{ij}2\frac{\alpha}{\sqrt{\pi}} \right] \qquad (15)$$

This new breakup of the potential leads to a subdivision of the forces on the basis of the distance over which they act, regardless of whether they are originally from real-space or k-space forces. Somewhat surprisingly, this can be implemented with less computation than for the real-space/k-space split described above. The full pair potential may, therefore, be given by $$V_{ij}^{el} = V_{ij}^0 + V_{ij}^n \qquad (16)$$

Note that the calculation of $V^n$ is nearly equivalent to the calculation of the fill Ewald k-space sum, with the substitution of a standard error function for its complement. Thus, $V^n$ is significantly more expensive to compute than $V^0$, which involves no special functions and can even be obtained at no cost during the time steps in which $V^n$ must be calculated. Furthermore, all of the terms in $V^n_{ij}$ are truly long-ranged, acting at distances beyond the cutoff in real space. This is the ideal situation for a RESPA split, since the most expensive part of the calculation is also the most long-ranged.

Using this division of the potential, a RESPA split can be defined which separates the "fast" force due to only the most short-ranged interactions $$F^{(f)}_{ij}=-S(r_{ij})\nabla r_{ij}V^0_{ij}+F^{LJ}_{ij} \qquad (17)$$

from the remaining "slow" forces $$F^{(s)}_{ij}=-[1-S(r_{ij})]\nabla r_{ij}V^0_{ij}-\nabla r_{ij}V^n_{ij} \qquad (18)$$

where the switching function S(r) is equal to unity at r=0, and smoothly decreases to zero beyond some cutoff distance. The use of a switching function is a common method used to minimize the energy conservation errors that are typically associated with abrupt cutoffs, such as the one implicit in $V^0_{ij}$ (R. Zhou and B. J. Berne, J. Chem. Phys. 103, 9444 (1995); M. E. Tuckerman, B. J. Berne, and G. J. Martyna, J. Chem. Phys. 94, 6811 (1991)). This subdivision of the forces can then be used in the force-split r-RESPA propagator outlined in the pseudocode above.

For solvated protein systems, the force (potential) can be expressed as a sum of several terms $$F(x)=F_{stret}(x)+F_{bend}(x)+F_{tors}(x)+F_{vdW}(x)+F_{elec}(x) \qquad (19)$$

where $F_{stret}$, $F_{bend}$, $F_{tors}$, $F_{vdW}$, and $F_{elec}$ represent the forces for stretching, bending, torsion, van der Waals, and electrostatic interactions respectively.

The forces may be separated according to their intrinsic differences in time scales.

$$F_0(x)=F_{stret}+F_{bend}(x)+F_{tors}(x) \qquad (20)$$

$$F_1(x)=F^{near}_{vdW}(x)+F^{near}_{elec}(x) \qquad (21)$$

$$F_2(x)=F^{med}_{vdW}(x)+F^{med}_{elec}(x) \qquad (22)$$

$$F_3(x)=F^{far}_{vdW}(x)+F^{far}_{elec}(x) \qquad (23)$$

The fast varying bonded forces are included in $F_0(x)$, the innermost "reference" propagator. The nonbonded forces are separated into three different shells, near-range ($F_1(x)$), intermediate range ($F_2(x)$), and far range ($F_3(x)$) according to the pair distance. In practice, $F_1(x)$ can be defined as van der Waals and real-space electronic forces with pair distance less than 7 Å, and $F_2(x)$ as van der Waals and real-space electrostatic forces with pair distance between 6 and 10 Å (there is some overlap due to the switching function applied between 6 and 7 Å.).

Procacci et al. took the outermost shell $F_3(x)$ to be the whole k-space electrostatic force (van der Waals forces can be omitted after 10 Å, since they are short-range forces) and later on also tried to break the real-space part in three regions (near, medium, and far), and then put the whole k-space contribution in the medium region of the real space (as explained below). However, this breakup is equivalent to the less efficient split discussed above and will be denoted as "RESPA1" below.

As explained above, the inventors have discovered that a better choice is to assign the entire Coulomb interaction between nearby atom pairs to the fast propagator, including both real- and k-space contributions. Forces acting between distant atoms (e.g., atoms in different periodic cells) can then be assigned to the slow propagator. Thus, all pair forces are subdivided on the basis of the distance over which they act, regardless of whether they are real-space or k-space forces as specified above. This split will be referred to as "RESPA2" below.

The notation used to indicate different combinations of time scale separation $(n_1, n_2, n_3)$ may be the same as in a previous paper (R. Zhou and B. J. Berne, J. Chem. Phys. 103, 9444 (1995)). That is, if the time step is $\delta t$ for bonded forces ($F_0(x)$), then the time step is $n_1 \delta t$ for near-region van der Waals and electrostatic forces ($F_1(x)$), $n_1 n_2 \delta t$ for medium-region van der Waals and electrostatic forces ($F_2(x)$), and $n_1 n_2 n_3 \delta t$ for medium-region van der Waals and electrostatic forces ($F_3(x)$) (R. Zhou and B. J. Berne, J. Chem. Phys. 103, 9444 (1995)).

Calculating Electrostatic Interactions

Mesh-based Ewald methods, including P3M Ewald (i.e., P3ME), provide an approximation to the reciprocal space term of the Ewald sum by assigning the point charges to a finite-sized grid. The other terms in the Ewald sum are left unchanged. The Fourier transforms used to evaluate the reciprocal space contribution are now reduced to the discrete finite Fourier transform (DFT). The DFT can be evaluated using the fast Fourier transform (FFT) algorithm (E. O. Brigham, *The Fast Fourier Transform* (Prentice-Hall, Englewood Cliffs, N.J., 1974)), the benefit being the FFT algorithm's favorable N log N scaling. If one chooses a large enough value for the Ewald parameter $\alpha$ (e.g., sufficiently small real space cutoff), the N log N scaling extends to the entire calculation.

The procedure for calculating the electrostatics using P3ME may consist of four steps as outlined by Deserno and Holm (M. Deserno and C. Holm, J. Chem. Phys. 109, 7678 (1998)): assigning charges to the grid, solving Poisson's equation on the grid, differentiation to determine the forces, and interpolating the forces on the grid back to particles. These items are covered in detail in Deserno's paper (M. Deserno and C. Holm, J. Chem. Phys. 109, 7678 (1998)). The procedure followed is highlighted hereinbelow.

Specifically, charges are assigned to mesh points using the assignment function W(x). The choice of W(x) used in all P3M methods is a spline scheme (R. W. Hockney and J. W. Eastwood, *Computer Simulations Using Particles* (IOP, Bristol, 1988)). The spline order P determines the number of grid points to which each charge is assigned in each coordinate direction. The weight functions up to order P=7 have been tabulated in a paper by Deserno (M. Deserno and C. Holm, J. Chem. Phys. 109, 7678 (1998)).

The second step involves solving Poisson's equation for the mesh-based charge density. Following the notation used by Hockney and Eastwood (R. W. Hockney and J. W. Eastwood, Computer Simulations Using Particles (IOP, Bristol, 1988)) one can define an influence function, $G(r_p)$, such that the potential on the mesh, $\Phi_M(r_p)$ is given by the inverse FFT of $$\tilde{\Phi}_M(k) = \tilde{G}(k)\tilde{\rho}_M(k) \tag{24}$$

where the function $\tilde{\rho}_M(k)$ is the finite Fourier transform of charge density $\rho_M(r_p)$. The choice of influence function G is a principal difference between the various mesh-based methods. The choice of G used for P3M in the original publication by Hockney and Eastwood (R. W. Hockney and J. W. Eastwood, Computer Simulations Using Particles (IOP, Bristol, 1988)), derived to minimize errors from discretization, was $$\tilde{G}_{opt}(k) = \frac{\tilde{D}(k) \cdot \sum_n \tilde{R}(k_n)[\tilde{W}(k_n)/V_c]^2}{|\tilde{D}(k)|^2 \left[\sum_n [\tilde{W}(k_n)/V_c]^2\right]^2} \tag{25}$$

The function $\tilde{D}(k_n)$ is the Fourier transform of the differential operator and depends on the differentiation scheme that is chosen. The function $\tilde{R}(k_n)$ is the Fourier transform of the true reference force $$\tilde{R}(k) = -ik\frac{4\pi}{k^2}e^{-k^2 4\alpha^2} \tag{26}$$

This optimized function $G_{opt}$ thus provided the closest mesh-based approximation to the continuous value assuming that finite difference differentiation is used to calculate the forces. It is important to note that if the differentiation method is not periodic, a more general form of the influence function should be used. Nevertheless, this form has been used even for nonperiodic differentiation schemes (M. Deserno and C. Holm, J. Chem. Phys. 109, 7678 (1998)).

The influence function used by the inventors [e.g., Eq. (27)] extends this $G_{opt}$ function to properly treat all differentiation methods (e.g., finite difference differentiation, differentiation in Fourier space, or gradient differentiation) for determining the forces (M. Deserno and C. Holm, J. Chem. Phys. 109, 7678 (1998)).

$$\tilde{G}_{opt}(k) = \frac{\sum_n \tilde{D}(k) \cdot \tilde{R}(k_n)[\tilde{W}(k_n)/V_c]^2}{\sum_n ([\tilde{W}(k_n)/V_c])^2 \sum_n |\tilde{D}(k_n)|^2 [\tilde{W}(k_n)/V_c]^2} \tag{27}$$

It is worth noting that Eq. (27) reduces to Eq. (25) only when the differential operator $\tilde{D}(k)$ is periodic in the alias sum over "n" and can therefore be taken out of the sum. This is valid when finite difference is used for the differentiation. However, using the nonperiodic continuous differential operator ik as employed by the Fourier and gradient methods of differentiation, discussed below, requires the form of $\tilde{G}$ given in Eq. (27).

In practice, force calculations by Deserno et al. (M. Deserno and C. Holm, J. Chem. Phys. 109, 7678 (1998)) using the incorrect form given by Eq. (25), still give more accurate results than both the PME and SPME methods. Correcting the influence function to that in Eq. (27) provides a further improvement to the force accuracy (the differences are, however, small and all but disappear for higher-order assignments and grid densities). Although somewhat complicated, $G_{opt}$ need only be precomputed at the outset of the simulation since there is no dependence on particle positions.

The RESPA split proposed by the inventors for the Ewald method is unchanged when replacing Ewald with the P3ME approximation. The P3ME approximation applies only to the reciprocal space term and thus has no effect on the division of the potential. The only difference will lie in choice of $\alpha$ and appropriate cutoffs that are to be used.

Experiments

The efficient MD algorithm proposed above can be applied to many biosystems, especially for those large proteins in explicit solvent molecules with periodic boundary conditions, which are unlikely to be accessible by standard methods due to limited computational resources today. For instance, the inventors have applied it to seven different sized solvated protein systems: a β-hairpin from protein G (2 gb 1) in 30.0 Å water box (2521 atoms), protein G (2 gb 1) in 36.0 Å water box (4276 atoms), CRO repressor insertion mutant (1 orc) in 42.0 Å water box (6911 atoms), H-ras P21 protein (121p) in 50.0 Å water box (11 717 atoms, L-*arabinose binding protein (8 abp) in 62.0 Å water box (22 716 atoms, and Fe-only hydrogenase (1 feh) in 84.0 Å water box (56 929 atoms). All the solvated protein systems were neutralized by adding counter ions, Na+ or Cl−, whenever the protein systems have net charges.

The details of these protein systems are summarized in Table 1 in FIG. 2. Specifically, FIG. 2 shows the protein systems used in the inventors' experiments. Each protein was solvated in a water box which was generated from a pre-equilibrated smaller water box, and then equilibrated for 30 ps with protein atoms frozen in space, and finally equilibrated for another 30 ps with all atoms relaxed.

More specifically, before performing a production MD run, some primary modifications should be applied to the initial x-ray or NMR structures from the PDB bank. First, all of the missing H atoms (possible missing heavy atoms too) are added to the protein systems by IMPACT. Then, a water box of specified size is generated from a pre-equilibrated smaller water box, and water molecules that overlap with the atoms on the protein are removed automatically. The solvated system is then minimized with the conjugate gradient method for a few hundred steps to remove any bad contacts due to the H-addition and water box generation. The minimized structure is then smoothly heated from 0 to 310K with all protein atoms fixed in space, so only water molecules are being equilibrated. After 30 ps of MD equilibration of the water, the protein atoms are also allowed to move and the total system is equilibrated from 0 to 310 K for another 30 ps. During this equilibration stage, the velocities are rescaled using the Berendsen velocity rescaling method (with relaxation time 0.01 ps), (H. J. C. Berendsen, J. P. M. Postma, W. F. van Gunsteren, and J. R. Haak, J. Chem. Phys. 81, 3684 (1984)), and are also periodically (every 1 ps) resampled by the Andersen (BGK) thermostat method (H. C. Andersen, J. Chem. Phys. 72, 2384 (1980)), i.e., resampled from the Maxwell-Boltzmann distribution at the target temperatures.

The accuracy of the P3M calculation is measured using the relative rms force error $$\Delta F = \sqrt{\frac{\sum_i ([F_i - F_i^{exact}])^2}{\sum_i (F_i^{exact})^2}} \quad (28)$$

where $F^{exact}$ is calculated by a well-converged Ewald sum and $F_i$ is the force on particle i calculated using P3ME. The RMS error $\Delta F$, is calculated for an equilibrated system of 2744 SPC water molecules in a cubic box of edge 43.5 Å with 10.0 Å cutoff in real space.

Figure 3A:
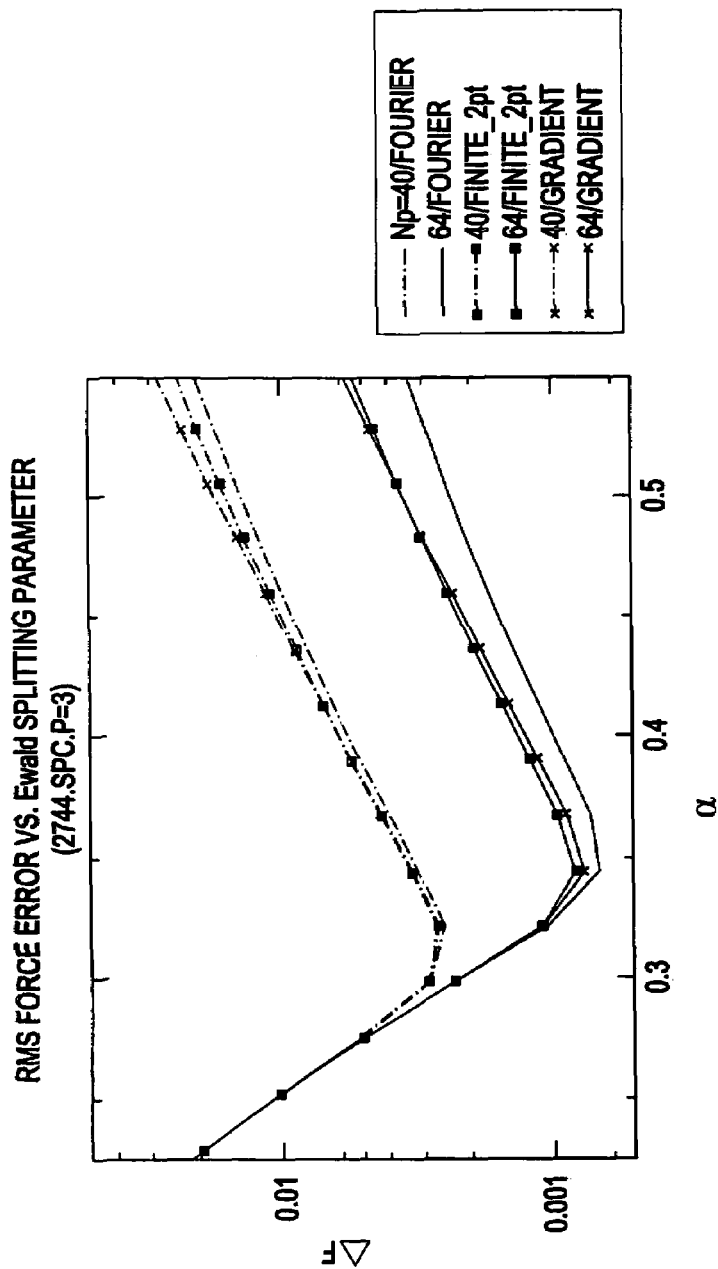
FIG. 3A is a graph illustrating a plot of ΔF as a function of the Ewald parameter α.
Figure 3B:
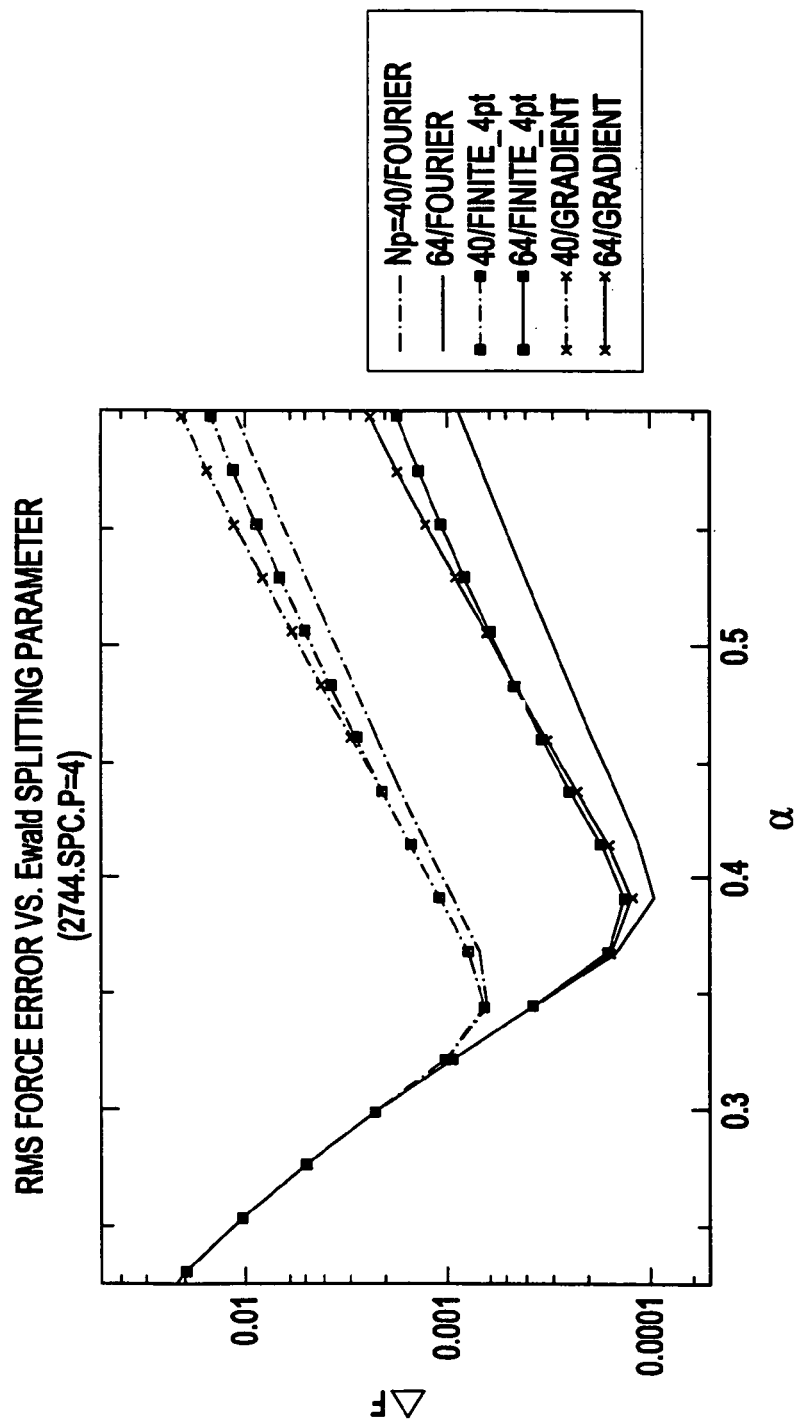
FIG. 3B is a graph illustrating a plot of ΔF as a function of the Ewald parameter α using P=4 spline.

The calculation of $\Delta F$ was carried out and plotted as a function of the Ewald parameter α in FIG. 3A. Generally, in FIG. 3A, the rms error $\Delta F$ (Eq. (28)) is shown for Np=40 (dash-dot line) and for Np=64 (solid line), where Np is the mesh size. Fourier space differentiation is without symbol, while gradient differentiation is represented by an "x" and finite 2-point differentiation uses the square symbol. All curves are calculated using the P=3 spline assignment scheme (calculations using P=4 spline are shown in FIG. 3B). The system is 2744 equilibrated SPC water molecules in a 43.5 Å cubic box.

More specifically, in FIG. 3A, the $\Delta F$ curves are calculated for various methods of differentiation, and mesh size $N_p$ equal to 44 (grid spacing 0.989 Å) and 88 (grid spacing 0.494 Å). The assignment scheme used to compute the curves in FIG. 3A is a third order spline (P=3). From FIG. 3A, it can be seen that by selecting α between 0.30 and 0.40 Å$^{-1}$, the relative rms force errors can be controlled well below $10^{-3}$ by using a grid spacing of 0.494 Å (mesh size 88). In the following solvated protein simulations, a gradient differentiation with a grid spacing of 0.50 Å was used, which always seems to be able to control $\Delta F$ to within $10^{-3}$, thereby guaranteeing a stable molecular dynamics integration (R. Zhou and B. J. Berne, J. Chem. Phys. 103, 9444 (1995)).

Figure 4A:
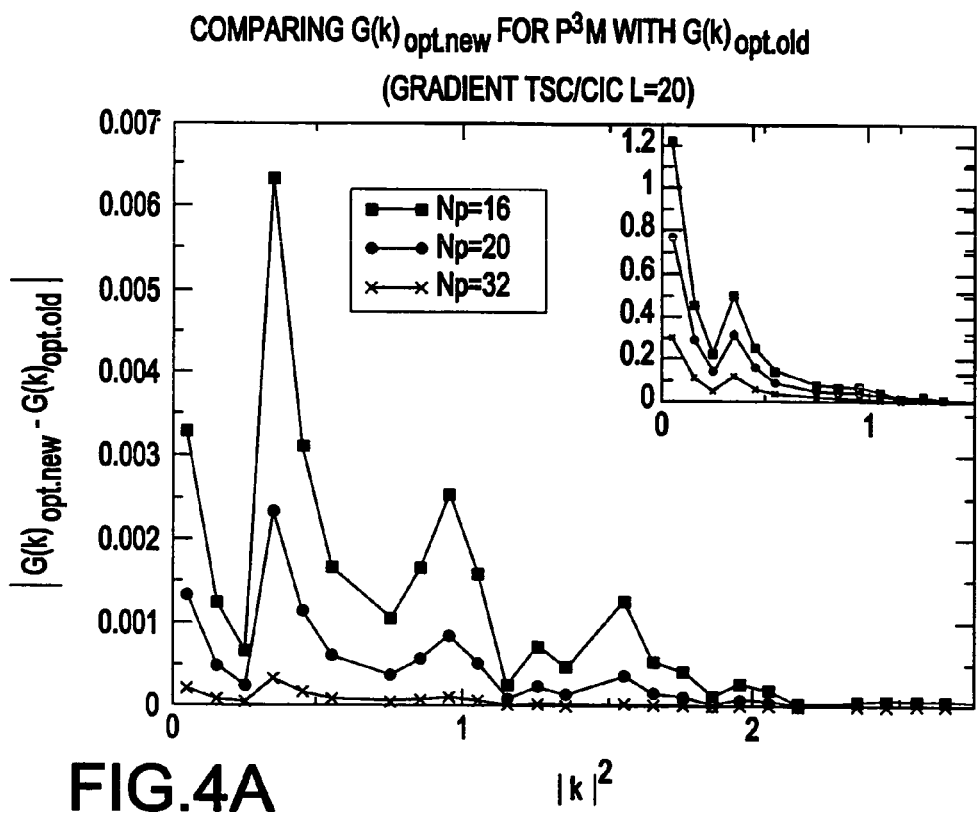
FIG. 4A is a graph illustrating a plot of the magnitude of the difference between the propagators against the square of the reciprocal space wave vector $|k|^2$.

The influence function used by the inventors (e.g., Eq. (27)), is compared to that used by Deserno, (Eq. (25)) in FIG. 4A, for differentiation using the ik operator. The inventors call the influence functional given in Eq. (27) $G_{opt.new}$ and in Eq. (25) $G_{opt.old}$. Generally, FIG. 4A shows the magnitude of difference between $G(k)_{optold}$ used in the paper by Deserno (e.g., Eq. (25)), and $G(k)_{optnew}$ used by the inventors (e.g,. Eq. (27)). The main plot is for P=3 order spline assignment scheme and the inset shows plot for P=2 order spline. Both plots show curves for grid sizes of Np=16, 20 and 32. Box length is 20 Å. It should be noted that the pronounced difference in the curves for P=2 assignment all but disappears for the P=3 assignment.

More specifically, FIG. 4A plots the magnitude of the difference between the propagators against the square of the reciprocal space wave vector |k|$^2$. (The difference is averaged over all k vectors whose magnitude is |k|.) The calculations are for mesh size $N_p$=16, 20, and 32, for a 20 Å water box. The old and new $G_{opt}$'s are compared for an assignment order P=3 (main) and P=2 (inset).

Figure 4B:
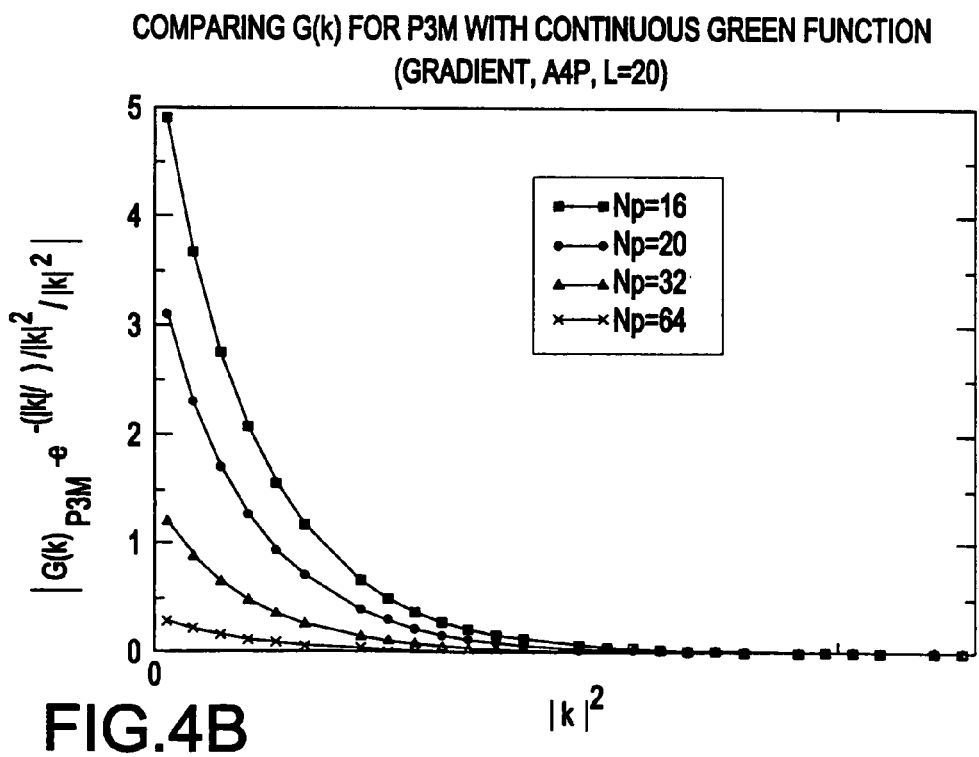
FIG. 4B is a graph illustrating a magnitude of difference between $G(k)_{opt}$ and $G(k)$ used in the PME method plotted against the square of the reciprocal wave vector.
Figure 4C:
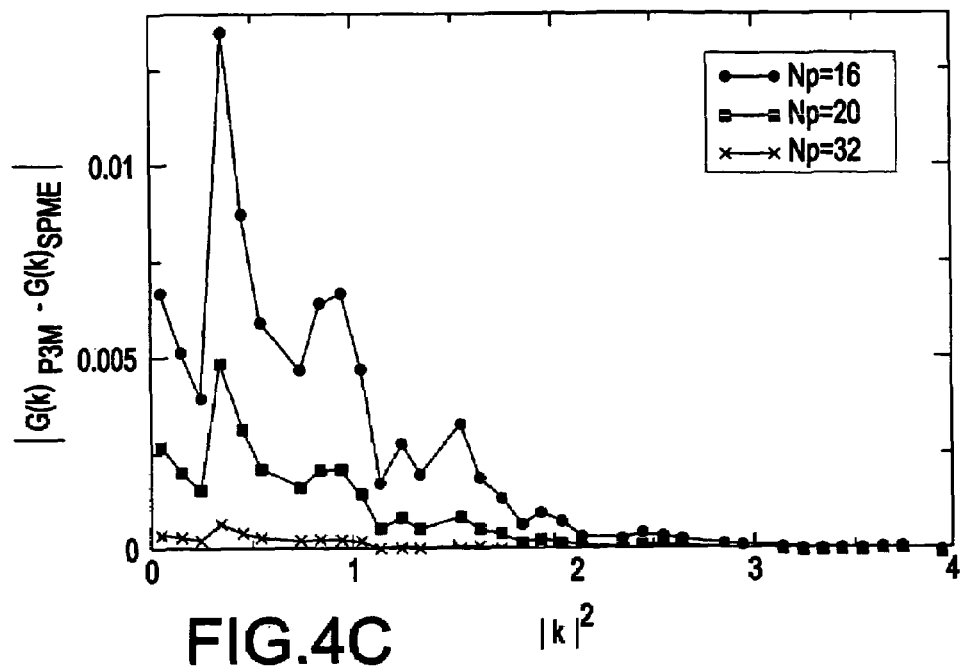
FIG. 4C is a graph illustrating a difference between optimized influence function and G(k) used in SPME method plotted against square of reciprocal wave vector.

FIG. 4B illustrates a magnitude of difference between $G(k)_{opt}$(Eq. (26)) and G(k) used in the PME method (Eq. (25)), |$G(k)_{opt}$−$G(k)_{PME}$|, plotted against the square of the reciprocal wave vector. The units of influence function are Å$^2$ kcal/e/mol. Further, FIG. 4C illustrates a difference between optimized influence function and G(k) used in SPME method plotted against square of reciprocal wave vector. The spline order for assignment used for each method shown in FIGS. 4B–4C is P=4. The box length is 20 Å. Curves for grid size of Np=16, 20 and 32 are shown.

Thus, there is a significant difference between the propagators for P=2 assignment for small |k|$^2$. It is clear that the P=2 spline should not be used with $G_{opt.old}$ [Eq. (25)] since the errors in the force calculation will be too large (R. W. Hockney and J. W. Eastwood, *Computer Simulations Using Particles* (IOP, Bristol, 1988)). The third-order spline is a more common method of assignment and the main plot in FIG. 4A shows how small the difference between the influence functions becomes. The convergence of the old and new $G_{opt}$ continues for higher assignment orders. This comparison displays the convergence of the influence functions for large grid densities. This is expected, since they should converge to the same continuous value for infinitesimal grid spacings. In the following simulations for protein systems, a grid spacing of 0.50 Å and P=3 will be used, unless otherwise explicitly specified.

In order to effectively compare various algorithms in MD, some accuracy measures for the MD simulations should be defined. Two energy conservation parameters are commonly used to describe the stability of a constant-energy MD simulation (D. D. Humphreys, R. A. Friesner, and B. J. Berne, J. Phys. Chem. 98, 6885 (1994); M. Watanabe and M. Karplus, J. Chem. Phys. 99, 8063 (1993)). One is the total energy fluctuation ΔE, defined by $$\Delta E = \frac{1}{N_T} \sum_{i=1}^{N_T} \left| \frac{E_0 - E_i}{E_0} \right| \tag{29}$$

where $E_i$ is the total energy at step i, $E_0$ is the initial energy, and $N_T$ is the total number of time steps. This quantity has been shown to be a reasonable measure of accuracy in previous simulations (F. Figueirido, R. Zhou, R. Levy, and B. J. Berne, J. Chem. Phys. 106, 9835 (1997); R. Zhou and B. J. Berne, J. Chem. Phys. 103, 9444 (1995); D. D. Humphreys, R. A. Friesner, and B. J. Berne, J. Phys. Chem. 98, 6885 (1994); and M. Watanabe and M. Karplus, J. Chem. Phys. 99, 8063 (1993)), and a value of ΔE≦0.003 (e.g., log (ΔE)<−2.5, gives an acceptable numerical accuracy). Another common measure of the accuracy is the ratio of the RMS deviation of the total energy to the RMS deviation of the kinetic energy (W. F. van Gunsteren and H. J. C. Berendsen, Mol. Phys. 34, 1311 (1977)).

$$R = \frac{\Delta E_{rms}}{\Delta KE_{rms}} \tag{30}$$

The inventors favor the parameter log (ΔE) over R, because the R value cannot effectively measure the total energy drift during MD simulations, while log (ΔE) is extremely sensitive to the energy drift.

In biomolecular simulations one typically subjects the system to holonomic constraints to keep the bond lengths fixed during the simulation. Moreover, many water models have been parameterized assuming rigid geometries. These constraints allow for larger time steps since the fast bond vibrations are frozen. The use of r-RESPA integrators, on the other hand, allows the use of a short time step for the rapidly varying bonding forces, and a large time step for the non-bonding forces, the most expensive part of calculations, less frequently.

However, since many force fields have been parameterized assuming rigid bonds, it is useful to allow for these constraints. Thus, the bond lengths were generally constrained to their equilibrium distances in the simulations performed by the inventors. Since it is only inside the innermost loop that the coordinates are updated, to satisfy the holonomic constraints, the inventors applied coordinate corrections with the SHAKE (J. P. Ryckaert, G. Ciccotti, and H. J. Berendsen, J. Comput, Chem. 23, 327 (1977)) algorithm. It would also be a simple matter to implement the more rigorous RATTLE method. It should be noted that when SHAKE (or SHAKE/RATTLE) is used, the resulting RESPA integrator is no longer reversible. Since the CPU time spent doing these updates scales linearly with the number of atoms, the overhead involved is negligible for large systems where the nonbonded force calculation may consume, for example, well over 90% of the time.

Figure 5:
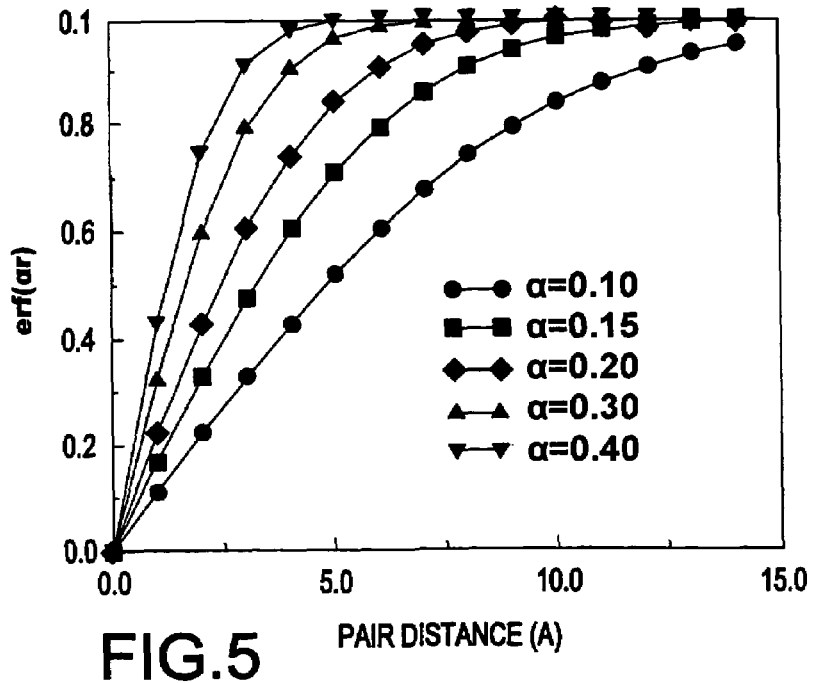
FIG. 5 is a graph illustrating a error function plotted against pair distance.

As briefly discussed above, the k-space forces of Ewald or other mesh-based Ewald methods have "short-ranged" contributions within them. To have a quantitative view of how the short-/long-range contributions are distributed in the reciprocal space, the inventors plotted the error function, erf(x)=1−erfc (x), where x=α$r_{ij}$ versus the pair distance $r_{ij}$ for α values ranging from 0.10 to 0.40 Å$^{-1}$ in FIG. 5. As shown in FIG. 5, when the parameter α increases, the complementary error function, erfc (α$r_{ij}$), decreases faster to zero with the pair distance. In other words, the error function, erf (α$r_{ij}$), increases faster to 1.0 with the pair distance.

Further, as mentioned above, the complementary error function portion of a Coulomb pair interaction is included in the real space, while the error function portion is included in the reciprocal space. Therefore, the bigger the erf(x), the larger the truly short-ranged contribution in the reciprocal-space forces. As shown in FIG. 5, at α=0.30 Å$^{-1}$ (most systems studied by the inventors will use α from 0.30 to 0.40 Å$^{-1}$ see below), more than 90% of the Coulomb interaction is calculated in the reciprocal space for a pair with pair distance of 5.0 Å. Even with an α as small as 0.1 Å$^{-1}$, there is still 52% contribution included in the reciprocal space for the same pair. This clearly shows that the reciprocal-space forces include "very short-ranged" contributions even for the nearest pairs in a typical force field. Thus, it can not be simply treated as "long-ranged" forces.

The inventors suspect that the authors of the previous approach have probably noticed this problem (P. Procacci, T. Darden, and M. Marchi, J. Phys. Chem. 100, 10464 (1996)), since they tried to put the whole reciprocal-space contribution in the middle of a three-stage real-space decomposition (0–5.3 Å, 4.3–7.3 Å, and 6.9–10.0 Å; there are some overlaps due to the switching function) to somewhat offset the influence from the short-range portion of the reciprocal-space forces. However, this approach makes the algorithm inefficient for at least two reasons: (a) in the reciprocal space, pairs closer than 10 Å are updated even less often than the truly long-range pairs more distant than 10 Å in the primary simulation box as well as contributions from all the distant replica boxes (e.g., for large solvated protein systems, these form the majority of the electrostatic interactions); and (b) in the Ewald method the expensive reciprocal-space forces are updated in the intermediate loop in RESPA.

Table II in FIG. 6 lists the detailed results for Ewald's combination with the two RESPA approaches. In particular, Table II provides a comparison of energy conservation and associated CPU times for Ewald Verlet, Ewald RESPA1 (real space and reciprocal-space decomposition), and Ewald RESPA2 (truly short-range and long-range decomposition). Δt (fs) is the overall time-step or the outermost time step (e.g., the innermost time step is 0.5 fs in RESPA), "n" represents the combinations of decomposition in RESPA1 and RESPA2, $T_{total}$ is the total CPU time which is collected from 1 ps MD runs for protein 121p on an International Business Machines (IBM) Power 3–200 MHz SP2 machine.

More specifically, in FIG. 6, the inventors selected L-*arabinose binding protein (8 abp, 22 716 atoms) as an example to illustrate the results. There are two parameters in the Ewald method, α and $k_{max}$. If one wants to use a short cutoff in the real-space sum, one needs to use a large α to converge the real space faster, but then the reciprocal space sum will converge slower, and more k vectors will be needed in the reciprocal-space sum, and vice versa. The optimized Ewald parameters will balance these two summations, and the typical values for α is about 5.5 /L (L is the box length)

and $k_{max}$ is about 5–10 (M. P. Allen and D. J. Tildesley, *Computer Simulation of Liquids* (Oxford University Press, Oxford, 1987)).

However, when coupling with RESPA, the inventors used a relatively short cutoff in the real space (10.0 Å), and used a larger a (from 0.30 to 0.40 Å$^{-1}$) and a larger $k_{max}$ (from 6 to 15), for two reasons. First, the RESPA algorithm will update the k-space forces less frequently, so the balance between the real space and k-space is biased to the k-space now. Second, particularly with respect to P3ME, since FFT is used in the P3ME method, which makes the k-space sum extremely fast, the inventors wanted to use a smaller cutoff in real space to balance the k-space part. So, in order to optimize Ewald and P3ME's real-space and k-space forces in this multiple time step "environment", the inventors adopted slightly different parameters from the normal Ewald optimization. For this protein, $\alpha$=0.35 and $k_{max}$=12 are used to get optimal results. RESPA 1 is denoted for the RESPA decomposition based on the real-space and k-space forces which was previously proposed by others, and RESPA2 is denoted for the inventive system 100 based on the true short-range and long-range contributions in Ewald sum.

As shown in Table II in FIG. 6, the Verlet algorithm shows poor energy conservation when the time step is increased above 2.0 fs. The total energy drifts even at this 2.0 fs time step, and the system blows up at a time step of 3.0 fs. RESPA1 can push the time step to 6 fs by using this log ($\Delta E$)<–2.5 criterion, and RESPA2 can go to time steps 9–12 fs with the same accuracy. The obvious reason for the smaller outer time step in RESPA1 is that there are truly short-range contributions to the reciprocal space forces and a small time step is thus required to handle these short-range contributions. In general, the time steps used in any RESPA subdivision should mimic the intrinsic time scales within the various force contributions. The RESPA2 algorithm accurately captures the short-range and long-range contributions to the electrostatic forces in the Ewald sum. Thus, a larger time step can be used in RESPA2 than in RESPA1.

Using Verlet with time step 1.0 fs as a benchmark for accuracy, the inventors compared the CPU times for the three algorithms, Verlet with time step 1.0 fs, RESPA1 with time step 6.0 fs, and RESPA2 with timestep 9.0 fs. The speedup of RESPA1 over Verlet is about 7.9 for this protein system, amounting to a factor of 2 speedup for RESPA2 over RESPA1 for Ewald coupling. This speedup comes mainly from two factors: (1) from the larger time step used, and (2) from the fact that the expensive evaluation of the error function or complementary error function is now included in the outermost loop in RESPA2 which is updated less often than in RESPA1.

FIG. 7 provides Table III which lists the CPU and energy conservation results for 8 abp using the P3ME method. In general, Table III provides a comparison of energy conservation and associated CPU times for P3ME/Verlet, P3ME/RESPA1 (real-space and reciprocal-space decomposition), and P3ME/RESPA2 (truly short-range and long-range decomposition). $\Delta t$ (fs) is the overall time-step or the outermost time step (e.g., the innermost time step is 0.5 fs in RESPA), "n" represents the combinations of decomposition in RESPA1 and RESPA2, $T_{total}$ is the total CPU time which is collected from 1 ps MD runs for protein 121p on an IBM Power 3–200 MHz SP2 machine.

As shown in Table III, except for the CPU timing, the energy conservation results are very close to those found from Ewald method. A grid spacing of 0.5 Å is used in P3ME for mesh generation, and the parameter $\alpha$=0.35 Å is used, which is the same as in Ewald method. An explicit $k_{max}$ is not necessary in the P3ME method, since it is implicitly included in the mesh generation for the FFT transformation. The gradient differentiator is used for the force calculations in P3ME. The relative rms force errors are always controlled within 10$^{-3}$ with respect to the Ewald method.

Again, with an accuracy level of log ($\Delta E$)<–2.5, a time step of 6 fs can be used in RESPA1, and 9–12 fs in RESPA2. Using P3ME/Verlet with a time step of 1.0 fs as benchmark, P3ME/RESPA1 with a time step of 6.0 fs and P3ME/RESPA2 with a time step of 9.0 fs can give comparable accuracies. The CPU speedup of RESPA1 and RESPA2 over Verlet is 3.3 and 4.8, respectively. Again, the CPU savings are from the bigger time step used in RESPA2, and the expensive error function evaluations being updated in the outermost loop. However, since the FFT routines used in P3ME is very fast, the overall CPU cost of the reciprocal space forces is much smaller than that in the Ewald method. This makes the CPU cost for real-space forces and bonded forces no longer negligible in the P3ME method, so the overall savings from RESPA in P3ME is not as impressive as in the Ewald case. Nevertheless, RESPA2 is still about 50% more efficient than RESPA1 for this case.

Figure 8:
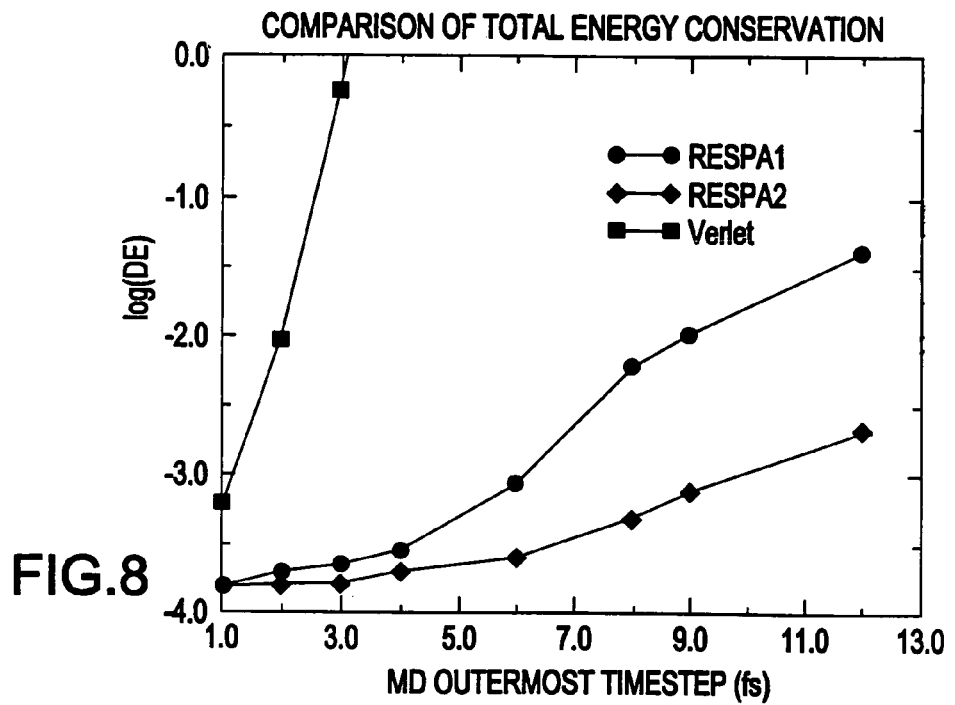
FIG. 8 is a graph illustrating energy conservation plotted versus time step used in the three algorithms, Verlet, RESPA1, and RESPA2.

A clearer view of the energy conservation versus time step used in the three algorithms, Verlet, RESPA1, and RESPA2 are also plotted in FIG. 8. The P3ME method is used for the calculation of the electrostatic interactions. As mentioned above, except for the CPU differences, there is little difference in the energy conservation in the Ewald or P3ME methods. In other words, the plot will look the same for the Ewald method.

As shown in FIG. 8, even with all the bond lengths being constrained with SHAKE, the Verlet algorithm still does not generate stable MD trajectories when the time step is increased beyond 2.0 fs, while RESPA algorithms allow one to use much larger time steps. RESPA2 is consistently better than RESPA1 for time steps starting from 2.0 fs for the reasons detailed above. This clearly shows that the time steps in the RESPA force decomposition have to closely follow the intrinsic time scales in the various force components. The truly short-range forces must be updated with smaller time steps, while the truly long-range forces can be updated with much larger time steps.

In order to quantify the savings in CPU time for various sized systems, the inventors studied a total of seven solvated proteins with sizes ranging from 2521 atoms to 56,926 atoms. The corresponding Verlet algorithm with time step of 1.0 fs was used as a benchmark for accuracy comparison in all cases. For most cases, RESPA1 uses a time step of 6.0 fs, and RESPA2 uses a time step of 9.0 fs. In the Ewald/RESPA methods, $\alpha$=0.35 Å$^{-1}$ with a real-space cutoff of 10 Å is used for various systems and $k_{max}$ varies from 6 ($\beta$-hairpin) to 15 (1 feh).

In addition, the P3ME/RESPA methods use the same $\alpha$ as in the Ewald sum for each system, and a fixed grid spacing of 0.5 Å is used for all systems to account for more k vectors in the Ewald sum for larger systems. The best possible results are reported for RESPA1 and RESPA2 when there are multiple choices for (n1, n2, n3) combinations for the same outermost time step. All the CPU timing is for 1.0 ps MD runs on IBM Power 3–200 MHz SP2 machines.

Figure 9:
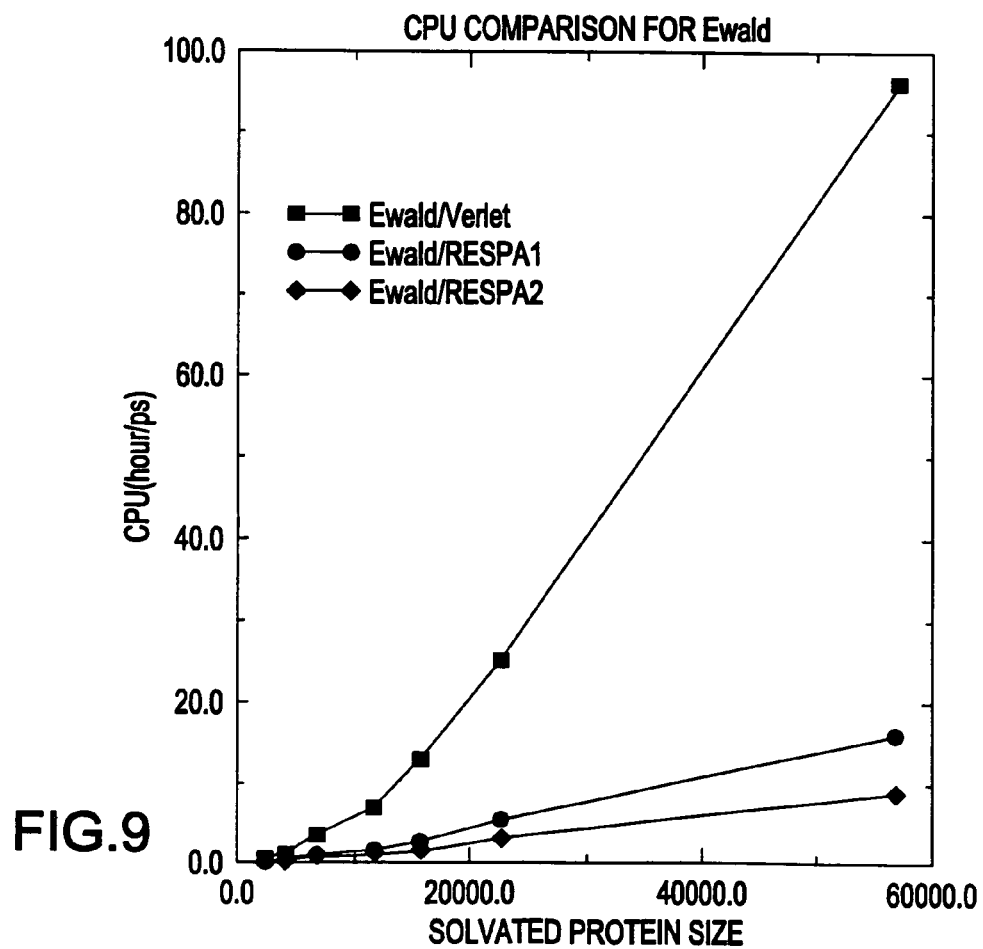
FIG. 9 is a graph illustrating the CPU timings for Ewald/Verlet, Ewald/RESPA1, and Ewald/RESPA2 for 1.0 ps MD of all seven protein systems.

FIG. 9 shows the CPU timings for Ewald/Verlet, Ewald/RESPA1, and Ewald/RESPA2 for 1.0 ps MD of all seven protein systems. Ewald/RESPA1 is about 3–5 times faster than Ewald/Verlet, and Ewald/RESPA2 is about 6–8 times faster than Ewald/Verlet with the same accuracy level of log ($\Delta E$)<–3.0. The CPU saving of RESPA vs. velocity Verlet springs from the fact that in RESPA, one can use a much larger time step than in velocity Verlet for the long-range nonbonded forces. The savings of RESPA2 over RESPA1 results from the reasons discussed above. The overall speedup of Ewald/RESPA2 is about a factor of 2 over the previously proposed Ewald/RESPA1.

Figure 10:
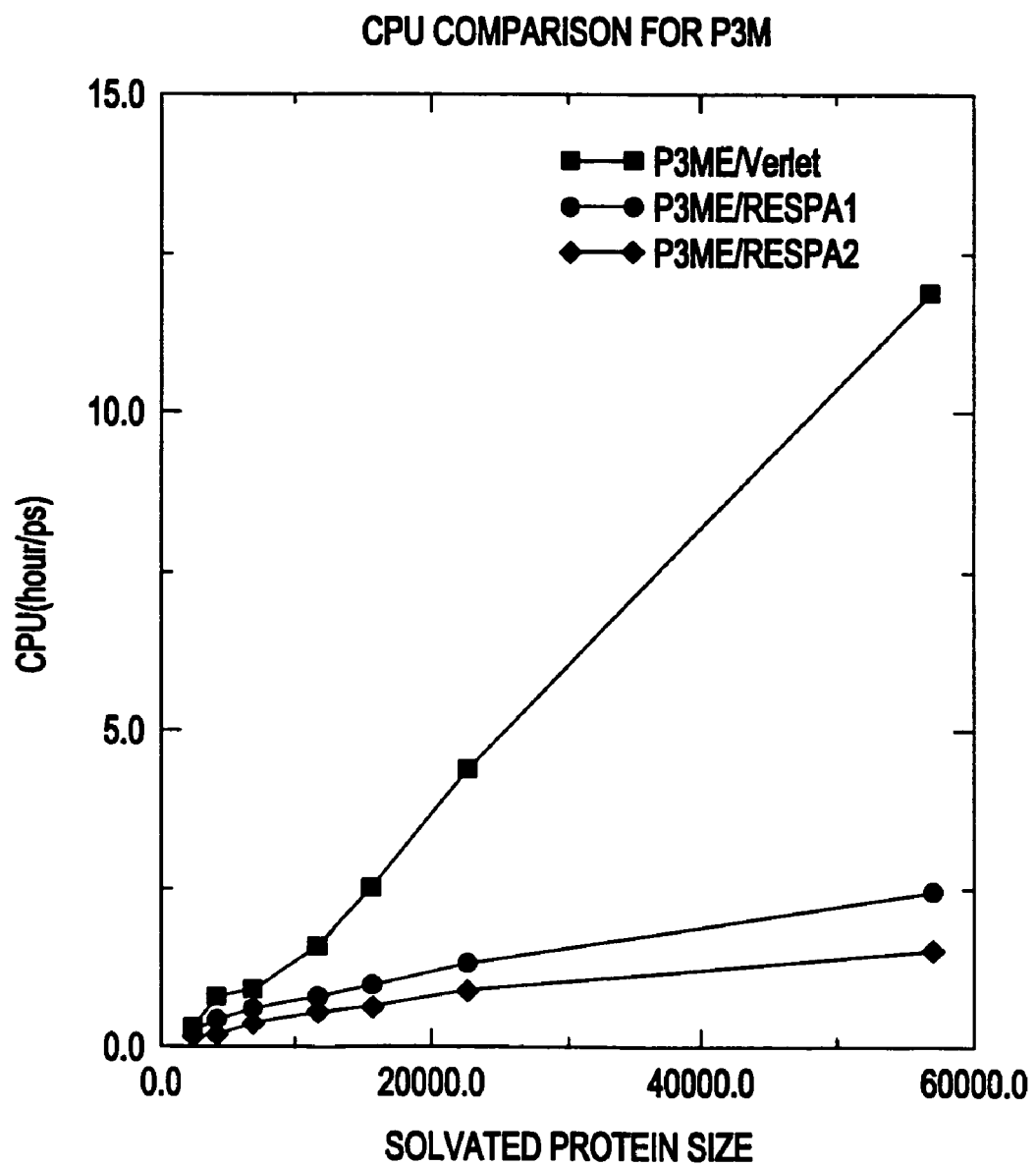
FIG. 10 is a graph illustrating a CPU comparison for P3ME/Verlet, P3ME/RESPA1, and P3ME/RESPA2.

The P3ME/Verlet, P3ME/RESPA1, and P3ME/RESPA2 comparisons are shown in FIG. 10. Similarly to those in the Ewald method, P3ME/RESPA1 is about 2–4 times faster than P3ME/Verlet, and P3ME/RESPA2 is 3–6 times faster than P3ME/Verlet. Compared to the RESPA speedup in the Ewald method, the RESPA speedup in P3ME is not as impressive because the CPU cost of FFT (the inventors used FFTW libraries from MIT) (M. Frigo and S. G. Johnson, http://www.fftw.org), which are very efficient) in P3ME is much smaller than the Ewald's reciprocal space summation for large systems. This results in a smaller difference between CPU times for the reciprocal-space vs. the real-space evaluations, since the CPU cost of the real-space part is the same in both Ewald and P3ME. Nevertheless, the inventive system 100 using RESPA2 approach for the RESPA decomposition is still about 50%–60% faster than the previous RESPA1 approach.

Figure 11:
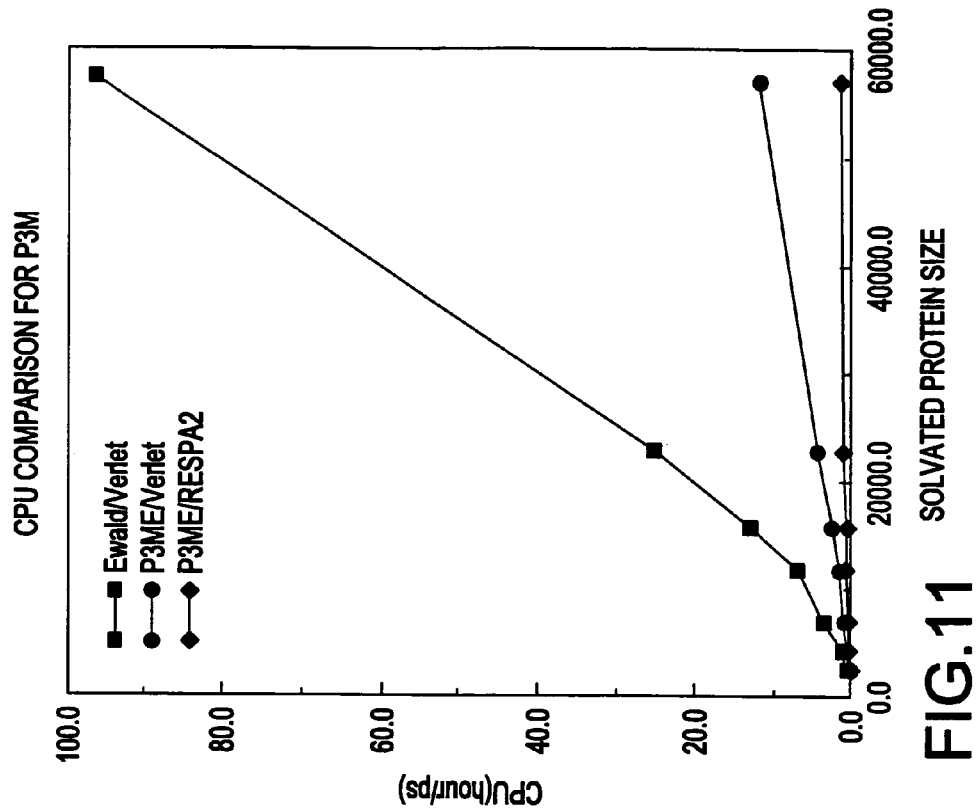
FIG. 11 is a graph illustrating the CPU comparison for Ewald/Verlet (which is probably the most commonly used algorithm), P3ME/Verlet, and P3ME/RESPA2 (an inventors' implementation of RESPA) in FIG. 11.

Further, in order to show how efficient the inventive system 100 and the new algorithm P3ME/RESPA2 is compared to the conventional algorithms widely used in MD packages, the inventors replotted the graphs for Ewald/Verlet (which is probably the most commonly used algorithm), P3ME/Verlet, and P3ME/RESPA2 (the inventors' implementation of RESPA) in FIG. 11. As shown in FIG. 11, the CPU speedups are dramatic from Ewald to P3ME and also dramatic from Verlet to RESPA. Using 1 feh as an example, the CPU cost is 96.15 h/ps for Ewald/Verlet, 11.87 h/ps for P3ME/Verlet, and 1.612 h/ps for P3ME/RESPA2. The speedup from P3ME for this system is about a factor of 8.1 and the total speedup from the coupling of P3ME with RESPA2 is about 59.6.

It should be pointed out that the inventors used a relatively high accuracy level, log ($\Delta E$)<-3.0, in the above CPU comparison for constant-energy simulations. If some loss of accuracy can be tolerated, such as log ($\Delta E$)<-2.5, something that might be desirable in constant-temperature MD simulations where velocities are rescaled and/or resampled periodically, an even larger speedup can be achieved in P3ME/RESPA2 by using time steps up to 12.0 fs.

Conclusion

As explained above, the inventive system 100 involves a new strategy for efficiently treating the multiple time scales and the long-range electrostatic forces encountered in aqueous solutions of proteins as well as in many other systems of interest to materials scientists. An aim of the inventive system 100 is to combine an inventive method for handling multiple time scales, for example, the RESPA method, with the Ewald and the particle-particle particle-mesh Ewald (or P3ME) method for efficiently calculating long-range electrostatic forces. Several years ago, the inventors outlined a strategy for breaking up the electrostatic forces in Ewald (and now in P3ME) such that only the fast (short-range) parts of the force are used in the short time propagator of RESPA and only the slow parts (long-range) are used in the long time step propagator. Thus, this suggestion was overlooked in papers in which RESPA was combined with Ewald and with particle mesh Ewald (PME).

The inventors refer to their new strategy as RESPA2 and the less efficient conventional strategy, RESPA1. When combined with Ewald the inventors refer to their new strategy as Ewald/RESPA2 and when combined with P3ME it is called P3ME/RESPA2. This new approach leads to a better partitioning of the reciprocal-space forces from the real-space forces in RESPA. It correctly separates the truly long-range contributions to the reciprocal space forces from the short-range forces in Ewald or P3ME, and performs the force decomposition based on the intrinsic short-/long range contributions in the electrostatic interactions rather than the more obvious real-space/reciprocal-space decompositions. The inventors found that the new partitioning used in Ewald/RESPA2 and P3ME/RESPA2 gives large improvements over Ewald/RESPA1 and P3ME/RESPA1. Since RESPA2 is no harder to use, and achieves larger speedups than RESPA1.

The P3M method, which scales as O(N log N) by using the fast Fourier transform (FFT) for the reciprocal-space interactions, is more efficient than the standard Ewald [$O(N^{3/2})$] method for simulation of biosystems with periodic boundary conditions. The inventors derived and used an improved influence function $G_{opt}$ [see, e.g., Eq. (27)]. This newly improved P3ME also gives more accurate results over previously proposed P3ME.

The timings performed by the inventors and discussed above, indicate that the Ewald/RESPA2 algorithm achieves approximately 6–8 times speedup over the Verlet algorithm for various solvated protein systems. The new approach achieves approximately double the speed of Ewald/RESPA1. The timings performed by the inventors and discussed above, indicate that P3ME/RESPA2 with the improved influence function is approximately 50%–60% faster than the previous approach with the same accuracy level.

The efficient combination of the P3ME method with the RESPA2 method results in an extremely fast molecular dynamics algorithm, which is about 60 times faster than the conventional method (e.g., Ewald with the Verlet integrator) for a solvated protein system with 57,000 atoms. Since the CPU saving in P3ME/RESPA2 comes from algorithmic improvements, one would expect comparable improvements in performance on platforms other than IBM SP2 machines, and also in a parallel computing environment.

Figure 12:
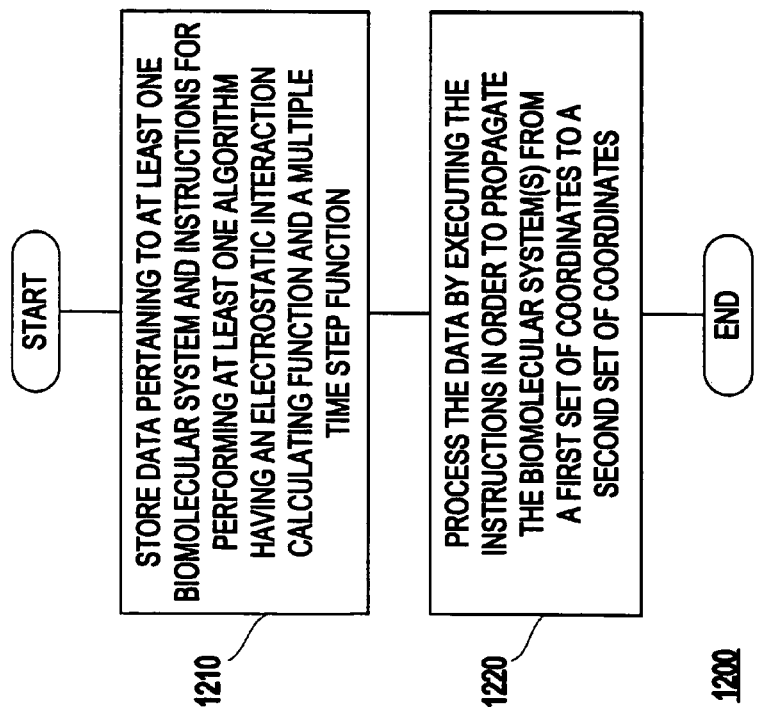
FIG. 12 is a flowchart illustrating the inventive method 1200 according to present invention.

In another aspect, the present invention includes an inventive method for molecular dynamic simulation 1200. As shown in FIG. 12, the inventive method 1200 includes storing (1210) data pertaining to at least one biomolecular system and instructions for performing at least one algorithm having an electrostatic interaction calculating function and a multiple time step function (e.g., a reversible reference system propagator (RESPA) function), and processing (1220) the data by executing the instructions in order to propagate the biomolecular system from a first set of coordinates to a second set of coordinates. (e.g., to generate a representation of electrostatic interactions). Specifically, the inventive method 1200 may be performed as described above with respect to the inventive system 100.

Figure 13:
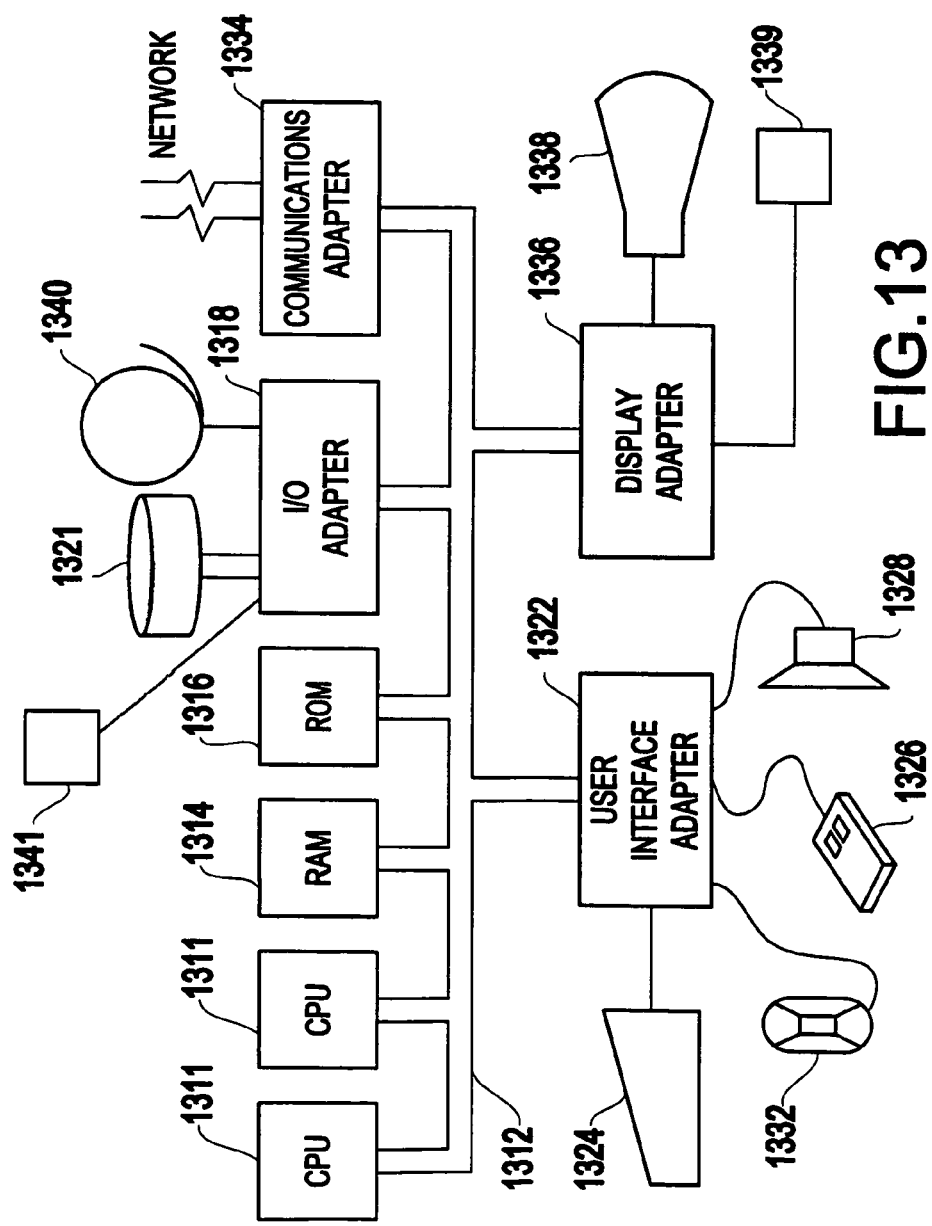
FIG. 13 illustrates a typical hardware configuration 1300 which may be used for implementing the present invention.

Referring now to FIG. 13, system 1300 illustrates a typical hardware configuration which may be used for implementing the inventive system and method for identifying genes. The configuration has preferably at least one processor or central processing unit (CPU) 1311. The CPUs 1311 are interconnected via a system bus 1312 to a random access memory (RAM) 1314, read-only memory (ROM) 1316, input/output (I/O) adapter 1318 (for connecting peripheral devices such as disk units 1321 and tape drives 1340 to the bus 1312), user interface adapter 1322 (for connecting a keyboard 1324, mouse 1326, speaker 1328, microphone 1332, and/or other user interface device to the bus 1312), a communication adapter 1334 for connecting an information handling system to a data processing network, the Internet, and Intranet, a personal area network (PAN), etc., and a display adapter 1336 for connecting the bus 1312 to a display device 1338 and/or printer 1339. Further, an automated reader/scanner 1341 may be included. Such readers/scanners are commercially available from many sources.

In addition to the system described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a programmed product, including signal-bearing media tangibly embodying a program of machine-readable instructions executable by a digital data processor to perform the inventive method.

Such a method may be implemented, for example, by operating the CPU 1311 to execute a sequence of machine-readable instructions. These instructions may reside in various types of signal bearing media.

Thus, this aspect of the present invention is directed to a programmed product, comprising signal-bearing media tangibly embodying a program of machine-readable instructions executable by a digital data processor incorporating the CPU 1311 and hardware above, to perform the method of the invention.

Figure 14:
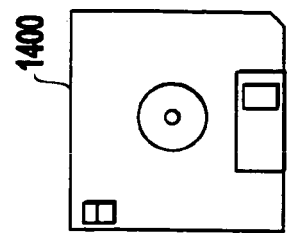
FIG. 14 illustrates a signal bearing medium 1400 for performing a method of molecular dynamic simulation according to the present invention.

This signal-bearing media may include, for example, a RAM contained within the CPU 1311, as represented by the fast-access storage for example. Alternatively, the instructions may be contained in another signal-bearing media, such as a magnetic data storage diskette 1400 (FIG. 14), directly or indirectly accessible by the CPU 1311.

Whether contained in the computer server/CPU 1311, or elsewhere, the instructions may be stored on a variety of machine-readable data storage media, such as DASD storage (e.g, a conventional "hard drive" or a RAID array), magnetic tape, electronic read-only memory (e.g., ROM, EPROM, or EEPROM), an optical storage device (e.g., CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, complied from a language such as "C," etc.

With its unique and novel features, the present invention provides a fast and accurate molecular dynamics simulation system and method. Unlike conventional algorithms which subdivide the Ewald or P3ME electrostatic forces into traditional real-space and k-space forces and then treat the forces as short-range (fast) and long-range (slow) forces, the present invention combines the force calculating function and multiple time step function (e.g., Ewald and RESPA) in an optimal way by "squeezing" the short-range contributions out of the k-space forces, thus making the modified "k-space" forces truly long-range (slow). This results in less computation time and a much more efficient system than conventional systems.

While the invention has been described in terms of preferred embodiments, those skilled in the art will recognize that the invention can be practiced with modification within the spirit and scope of the appended claims. For instance, it is understood that data pertaining to a biomolecular system may be stored in a remote database and remotely input to the inventive system 100. For instance, such data may be stored in a remote database and transmitted over the Internet (e.g., World Wide Web) to be processed by the inventive system 100. Further, it is understood that such data may be stored in the same memory device which stores the instructions for executing the algorithm for processing the data.

What we claim is:

1. A system for molecular dynamic simulation, comprising:
    a database for storing data pertaining to at least one biomolecular system;
    a memory device for storing instructions for performing at least one algorithm having an electrostatic interaction calculating function using a P3ME algorithm, and a multiple time step function, and subdividing forces based on distances over which said forces act; and
    a processor for processing said data by executing said instructions in order to propagate said at least one biomolecular system from a first set of coordinates to a second set of coordinates,
    wherein said processing comprises combining k-space electrostatic interactions calculated using said P3ME algorithm with said multiple time step algorithm using a mechanism which removes the short-range portion from said calculated k-space electrostatic interactions and updates said portion along with other short-range forces in said multiple time step algorithm.

2. The system for molecular dynamic simulation according to claim 1, wherein said forces are subdivided on a basis of distance over which said forces act regardless of whether said forces are real-space or k-space forces.

3. The system for molecular dynamic simulation according to claim 1, wherein said at least one algorithm comprises a first portion which separates long-range contributions to reciprocal space forces from short range forces, and a second portion which performs force decomposition based on intrinsic short and long range contributions in said electrostatic interactions.

4. The system for molecular dynamic simulation according to claim 1, wherein said at least one algorithm computes a sum of short range electrostatic interactions by the equation $$V_{ij}^0 = (1 - \delta_{ij})q_i q_j \frac{1}{r_{ij}} h(r_{ij}),$$

where $\delta_{ij}$ is the Dirac delta function with a value of 1 if i=j and 0 otherwise, $q_i$ and $q_j$ are charges associated with particles i and j, respectively, $r_{ij}$ is pair distance, and $h(r_{ij})=1$ if $r_{ij} \leq L/2$ and $h(r_{ij})=0$ if $r_{ij} \geq L/2$, where L is a minimum image cutoff.

5. The system for molecular dynamic simulation according to claim 1, wherein said at least one algorithm computes a sum of long range electrostatic interactions by the equation $$V_{ij}^n = q_i q_j \left[ -(1-\delta_{ij})\frac{\text{erf}(\alpha r_{ij})}{r_{ij}} h(r_{ij}) + \frac{1}{\pi L^3} \sum_{k \neq 0} \frac{4\pi^2}{k^2} e^{-k^2/4\alpha^2} \cos(k \cdot r_{ij}) - \delta_{ij}\frac{2\alpha}{\sqrt{\pi}} \right]$$

where $q_i$ and $q_j$ are charges associated with particles i and j, respectively, $\delta_{ij}$ is the Dirac delta function with value of 1 is i=j and 0 otherwise, $\alpha$ is a screening parameter, $r_{ij}$ is a pair distance, and $h(r_{ij})=1$ if $r_{ij} \leq L/2$ and $h(r_{ij})=0$ if $r_{ij} \geq L/2$, where L is a minimum image cutoff, and k is k-space vector magnitude.

6. The system for molecular dynamic simulation according to claim 1, wherein said at least one algorithm computes a full pair potential by the equation $V^{el}_{ij}=V^0_{ij}+V^n_{ij}$ where $V^0_{ij}$ is the sum of the short range electrostatic interactions and $V^n_{ij}$ is the sum of the long range electrostatic interactions.

7. The system for molecular dynamic simulation according to claim 1, wherein said processor generates a representation of electrostatic interactions.

8. The system for molecular dynamic simulation according to claim 1, wherein said at least one algorithm comprises an Ewald and reversible reference propagator (Ewald/RESPA) algorithm.

9. The system for molecular dynamic simulation according to claim 1, wherein said at least one algorithm comprises a particle-particle particle-mesh Ewald and reversible reference propagator (P3ME/RESPA) algorithm.

10. The system for molecular dynamic simulation according to claim 1, wherein said electrostatic interactions comprise short-range and long-range electrostatic forces.

11. The system for molecular dynamic simulation according to claim 1, further comprising:
a display device for displaying a result generated by said processor.

12. The system for molecular dynamic simulation according to claim 1, further comprising:
an input device for inputting said data.

13. The system for molecular dynamic simulation according to claim 1, wherein said multiple time step function comprises a force-based split RESPA function.

14. The system of claim 1, wherein said processing comprises adding said short range portion of said calculated k-space electrostatic interactions to a short range portion of real space electrostatic interactions.

15. The system of claim 1, wherein said short range portion of said calculated k-space electrostatic interactions is given by the equation $$\Delta = (1-\delta_{ij})\frac{q_i q_j}{r_{ij}} \text{erf}(\alpha r_{ij}) h(r_{ij}),$$

where $q_i$ and $q_j$ are charges associated with particles i and j, respectively, $\delta_{ij}$ is the Dirac delta function with value of 1 if i=j and 0 otherwise, $\alpha$ is a screening parameter, $r_{ij}$ is pair distance, and $h(r_{ij})=1$ if $r_{ij} \leq L/2$ and $h(r_{ij})=0$ if $r_{ij} \geq L/2$, where L is a minimum image cutoff.

16. The system of claim 15, wherein said processing comprises adding said short range portion of said calculated k-space electrostatic interactions to short range electrostatic interactions which were separated by said multiple time step function to calculate total short range electrostatic interactions.

17. The system of claim 1, wherein said and subdividing said forces comprises splitting non-bonded forces into a plurality of regions based on pair distances using switching functions.

18. A method for molecular dynamic simulation, comprising:
storing data pertaining to at least one biomolecular system and instructions for performing at least one algorithm having an electrostatic interaction calculating function using a P3ME algorithm, and a multiple time step function, and subdividing forces on a basis of distances over which said forces act; and
processing said data by executing said instructions in order to propagate said at least one biomolecular system from a first set of coordinates to a second set of coordinates,
wherein said processing comprises combining k-space electrostatic interactions calculated using said P3ME algorithm with said multiple time step algorithm using a mechanism which removes a short range portion from said calculated k-space electrostatic interactions and updates said portion along with other short-range forces in said multiple time step algorithm.

19. The method for molecular dynamic simulation according to claim 18, wherein said at least one algorithm computes a sum of short range electrostatic interactions by the equation $$V_{ij}^0 = (1-\delta_{ij}) q_i q_j \frac{1}{r_{ij}} h(r_{ij}),$$

where $\delta_{ij}$ is the Dirac delta function with value of 1 if i=j and 0 otherwise, $q_i$ and $q_j$ are charges associated with particles i and j, respectively, $r_{ij}$ is a pair distance, and $h(r_{ij})=1$ if $r_{ij} \leq L/2$ and $h(r_{ij})=0$ if $r_{ij} \geq L/2$, where L is a minimum image cutoff.

20. The method for molecular dynamic simulation according to claim 18, wherein said at least one algorithm computes a sum of long range electrostatic interactions by the equation $$V_{ij}^n = q_i q_j \left[ -(1-\delta_{ij})\frac{\text{erf}(\alpha r_{ij})}{r_{ij}} h(r_{ij}) + \frac{1}{\pi L^3} \sum_{k \neq 0} \frac{4\pi^2}{k^2} e^{-k^2/4\alpha^2} \cos(k \cdot r_{ij}) - \delta_{ij}\frac{2\alpha}{\sqrt{\pi}} \right]$$

where $q_i$ and $q_j$ are charges associated with particles i and j, respectively, $\delta_{ij}$ is the Dirac delta function with value of 1 if i=j and 0 otherwise, $\alpha$ is a screening parameter, $r_{ij}$ is pair distance, and $h(r_{ij})=1$ if $r_{ij} \leq L/2$ and $h(r_{ij})=0$ if $r_{ij} \geq L/2$, where L is a minimum image cutoff, and k is k-space vector magnitude.

21. The method for molecular dynamic simulation according to claim 18, wherein said at least one algorithm computes a full pair potential by the equation $$V^{el}_{ij} = V^0_{ij} + V^n_{ij}$$

where $V^0_{ij}$ is the sum of the short range electrostatic interactions and $V^n_{ij}$ is the sum of the long range electrostatic interactions.

22. The method for molecular dynamic simulation according to claim 18, wherein said at least one algorithm comprises a particle-particle particle-mesh Ewald and reversible reference propagator (P3ME/RESPA) algorithm.

23. The method for molecular dynamic simulation according to claim 18, wherein said processing said data comprises generating a representation of electrostatic interactions.

24. A method for molecular dynamic simulation, comprising:
- separating bonded interactions from non-bonded interactions using a multiple time step algorithm;
- separating said non-bonded interactions into short-range, midrange, and long-range interactions using said multiple time step algorithm;
- using a P3ME algorithm to calculate k-space electrostatic interactions; and
- combining said calculated k-space electrostatic interactions with said multiple time step algorithm using a mechanism which removes the short range portion from said calculated k-space electrostatic interactions and updates said portion along with other short-range forces in said multiple time step algorithm, to propagate a protein system.

25. A system for molecular dynamic simulation, comprising:
- a module for separating bonded interactions from non-bonded interactions using a multiple time step algorithm;
- a module for separating said non-bonded interactions into short-range, midrange, and long-range interactions using said multiple time step algorithm;
- a module for using a P3ME algorithm to calculate k-space electrostatic interactions; and
- a module for combining said calculated k-space electrostatic interactions with said multiple time step algorithm using a mechanism which removes the short range portion from said calculated k-space electrostatic interactions and updates said portion along with other short-range forces in said multiple time step algorithm, to propagate the protein system.

26. A programmable storage medium tangibly embodying a program of machine-readable instructions executable by a digital processing apparatus to perform a method for molecular dynamic simulation, said method comprising:
- storing data pertaining to at least one biomolecular system and instructions for performing at least one algorithm having an electrostatic interaction calculating function using a P3ME algorithm, and a multiple time step function; and
- processing said data by executing said instructions in order to propagate said at least one biomolecular system from a first set of coordinates to a second set of coordinates,
- wherein said processing comprises combining k-space electrostatic interactions calculated using said P3ME algorithm with said multiple time step algorithm using a mechanism which removes the short range portion from said calculated k-space electrostatic interactions and updates said portion along with other short-range forces in said multiple time step algorithm.

27. A programmable storage medium tangibly embodying a program of machine-readable instructions executable by a digital processing apparatus to perform a method for molecular dynamic simulation, said method comprising:
- separating bonded interactions from non-bonded interactions using a multiple time step algorithm;
- separating said non-bonded interactions into short-range, midrange, and long-range interactions using said multiple time step algorithm;
- using a P3ME algorithm to calculate magnitudes of k-space electrostatic interactions; and
- combining said calculated k-space electrostatic interactions with said multiple time step algorithm using a mechanism which removes the short range portion from said calculated k-space electrostatic interactions and updates said portion along with other short-range forces in said multiple time step algorithm, to propagate a protein system.

* * * * *